(12) United States Patent
Kudo

(10) Patent No.: US 11,457,878 B2
(45) Date of Patent: Oct. 4, 2022

(54) INTERIOR CT IMAGE GENERATION METHOD

(71) Applicant: University of Tsukuba, Ibaraki (JP)

(72) Inventor: Hiroyuki Kudo, Tsukuba (JP)

(73) Assignee: UNIVERSITY OF TSUKUBA, Tsukuba (JP)

( * ) Notice: Subject to any disclaimer, the term of this patent is extended or adjusted under 35 U.S.C. 154(b) by 468 days.

(21) Appl. No.: 16/495,904

(22) PCT Filed: Feb. 9, 2018

(86) PCT No.: PCT/JP2018/004603
§ 371 (c)(1),
(2) Date: Sep. 20, 2019

(87) PCT Pub. No.: WO2018/179905
PCT Pub. Date: Oct. 4, 2018

(65) Prior Publication Data
US 2020/0029917 A1 Jan. 30, 2020

(30) Foreign Application Priority Data
Mar. 27, 2017 (JP) ................. 2017-061390

(51) Int. Cl.
*A61B 6/03* (2006.01)
*A61B 6/00* (2006.01)
*G06T 11/00* (2006.01)

(52) U.S. Cl.
CPC ............ *A61B 6/032* (2013.01); *A61B 6/4078* (2013.01); *A61B 6/469* (2013.01); *G06T 11/005* (2013.01);
(Continued)

(58) Field of Classification Search
CPC ....... A61B 6/032; A61B 6/4078; A61B 6/469; G06T 11/005; G06T 11/006;
(Continued)

(56) References Cited
U.S. PATENT DOCUMENTS 6,246,742 B1 * 6/2001 Besson ................. G06T 11/005
378/15
7,697,658 B2 4/2010 Wang et al.
(Continued)

FOREIGN PATENT DOCUMENTS

| JP | 52-110581 A | 9/1977 |
| JP | 11-019078 A | 1/1999 |
| JP | 2003-502130 A | 1/2003 |

OTHER PUBLICATIONS

Sharma et al., "Scout-view Assisted Interior Micro-CT" 2013 Phys Med. Biol, pp. 4297-4314 (Year: 2013).*
(Continued)

*Primary Examiner* — Courtney D Thomas
(74) *Attorney, Agent, or Firm* — Mattingly & Malur, PC

(57) ABSTRACT

An image generation method of an interior CT includes the following steps: a step for obtaining interior CT projection data by measuring quantum beams passing through a region of interest (ROI) in an inside of photographing object in a geometrical system for CT measurement; a step for obtaining partial entire projection data by measuring quantum beams passing through an entire of said photographing object from a segment in an outside of said photographing object in said geometrical system for CT measurement; and a processing step for exactly reconstructing said ROI upon basis of said interior CT projection data obtained and said partial entire projection data.

14 Claims, 22 Drawing Sheets

(52) U.S. Cl.
CPC ....... *G06T 11/006* (2013.01); *G06T 2211/416* (2013.01); *G06T 2211/432* (2013.01)

(58) Field of Classification Search
CPC ......... G06T 2211/416; G06T 2211/432; G06T 2211/421
See application file for complete search history.

(56) References Cited

U.S. PATENT DOCUMENTS

| | | | |
|---|---|---|---|
| 8,811,700 B2 | 8/2014 | Wang et al. | |
| 2009/0196393 A1* | 8/2009 | Wang | A61B 6/508 378/4 |
| 2011/0142316 A1 | 6/2011 | Wang et al. | |

OTHER PUBLICATIONS

Extended European Search Report received in corresponding European Application No. 18776469.1 dated Dec. 1, 2020.
Sharma, K. et al., "Scout-view assisted interior micro-CT", Phys. Med. Biol., 2013, pp. 4297-4314, vol. 58, No. 12.
Nang, G. et al., "Topical Review; The meaning of interior tomography", Phys. Med. Biol., 2013, pp. R161-R186, vol. 58, No. 16.
Ogawa, et al. "A Reconstruction Algorithm from Truncated Projections", IEEE Transactions on Medical Imaging, vol. MI-3, No. 1, Mar. 1984, pp. 34-40.
Natterer F: "The Mathematics of Computerized Tomography", Wiley, pp. 169-173, 1986.
Ogawa, et al. "A Reconstruction Algorithm from Truncated Projections", IEEE Transactions on Medical Imaging, vol. MI-3, No. 1, Mar. 1987, pp. 34-40.
B. Ohnesorge, et al., "Efficient correction for CT image artifacts caused by objects extending outside the scan field of view". Medical Physics, vol. 27, No. 1, Jan. 2000, pp. 39-46.
Nagaaki Ohyama, et al., "Analysis and improvement in region-of-interest tomography", Applied Optics, vol. 23, No. 22, Nov. 15, 1984, pp. 4105-4110.
Yangbo Ye, et al., "A General Local Reconstruction Approach Based on a Truncated Hilbert Transform", International Journal of Biomedical Imaging, vol. 2007, Article ID 63634, 8 Pages.
Hiroyuki Kudo, et al., "Tiny a priori knowledge solves the interiorproblem in computed tomography", Physics in Medicine and Biology, 53, 2008, pp. 2207-2231.
Hengyong Yu, et al., "Compressed sensing based interior tomography", Physics in Medicine and Biology, 54, Apr. 15, 2009, pp. 2791-2805.
Jiansheng Yang, et al., "High-order total variation minimization for interior tomography", Inverse Problems, 26: ArticleID 35013, 2010.
Hiroyuki Kudo, et al., Practical interior tomography, Proceedings of International Forum on Medical Imaging in Asia (IFMIA) 2017, Paper No. 07-I-2, pp. 76-80, 2017.
Alexander Katsevich, "Analysis of an exact inversion algorithm for spiral cone-beam CT", Physics in Medicine and Biology, 47, Jul. 17, 2002, pp. 2583-2597.
Frederic Noo, et al., "Image reconstruction from fan-beam projections on less than a short scan", Physics in Medicine and Biology 47, Jul. 4, 2002, pp. 2525-2546.
Atsushi Momose, "Phase-Contrast X-ray Imaging", Synchrotron Radiation, 10, 1997, pp. 273-285.
International Search Report of PCT/JP2018/004603 dated Apr. 24, 2018.

* cited by examiner

FIG. 3A
HEAD OF HUMAN BODY
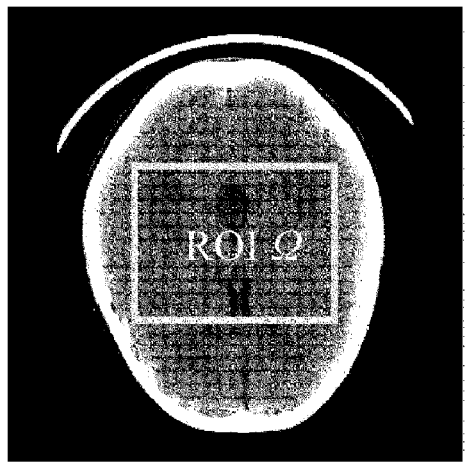 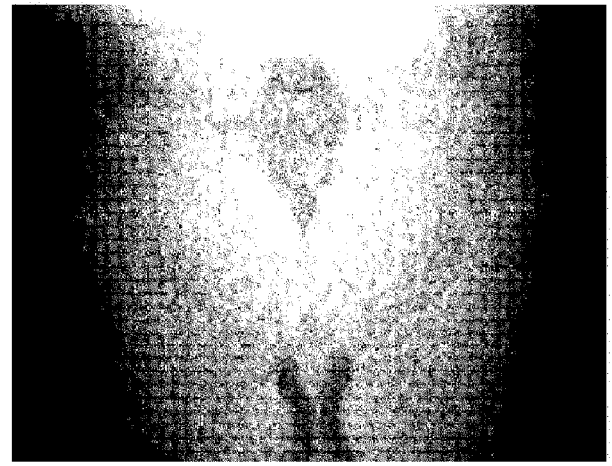
RECONSTRUCT FROM ENTIRE PROJECTION DATA
SHADING ARTIFACT
RECONSTRUCT FROM INTERIOR CT PROJECTION DATA
FIG. 3B
LUNGS OF MOUSE
(SYNCHROTRON RADIATION CT)
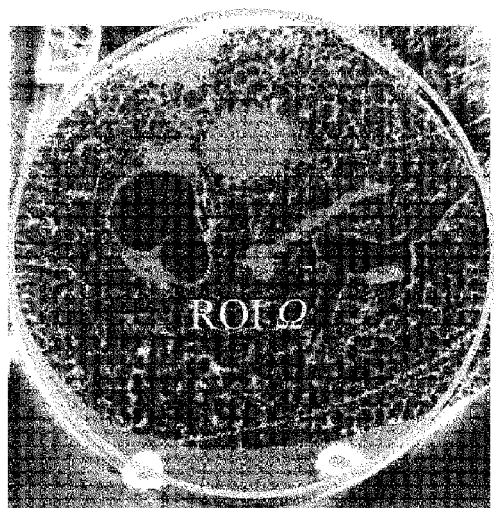 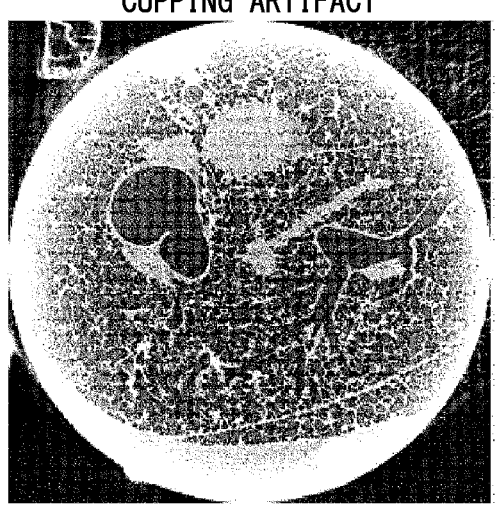
RECONSTRUCT FROM ENTIRE PROJECTION DATA
CUPPING ARTIFACT
RECONSTRUCT FROM INTERIOR CT PROJECTION DATA

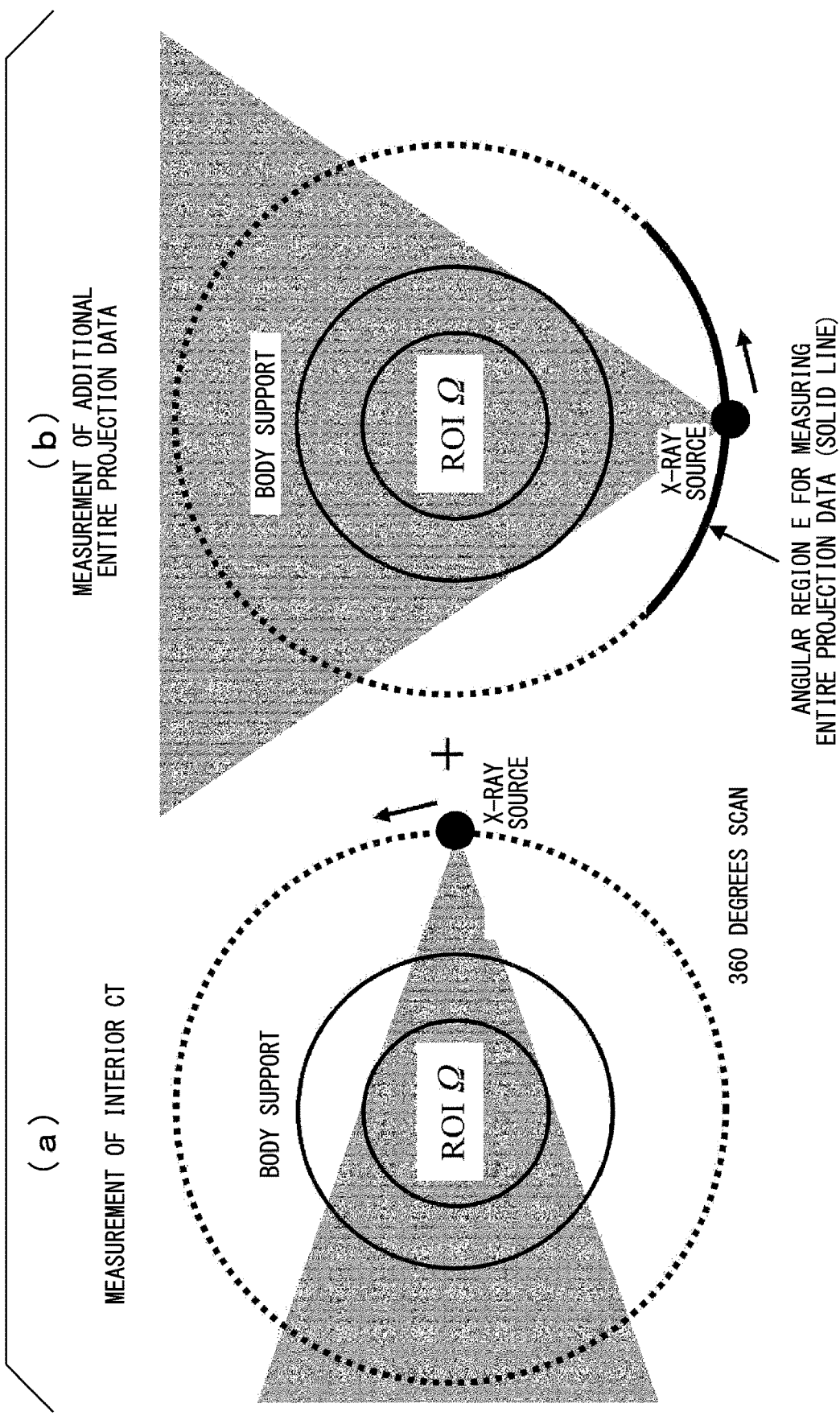

180 DEGREES PARALLEL BEAM SCAN

FAN BEAM SHORT SCAN

ORDINARY CT (RADIATE X-RAYS ON ENTIRE OBJECT)

INTERIOR CT (RADIATE ONLY X-RAYS PASSING THROUGH ROI Ω)

SYMMETRY OF FILTER CORRECT PROJECTION DATA $g^F(u, \beta)$ $$g^F(u_0, \beta_0) = g^F(u_1, \beta_1)$$

HILBERT TRANSFORM BY USING PRIOR INFORMATION IN TRUNCATION DATA

GEOMETRIC DISPOSITION WHEREIN X-RAY SOURCE ORBIT,
BODY SUPPORT AND ROI $\Omega$ ARE NOT CONCENTRIC

ANGULAR RANGE E (SOLID LINE)
FOR MEASURING ENTIRE PROJECTION DATA

GEOMETRIC DISPOSITION OF CONVEX-SHAPED REGION WHERE
BODY SUPPORT AND ROI $\Omega$ ARE ARBITRARY

ANGULAR RANGE E (SOLID LINE)
FOR MEASURING ENTIRE PROJECTION DATA

FIG. 15
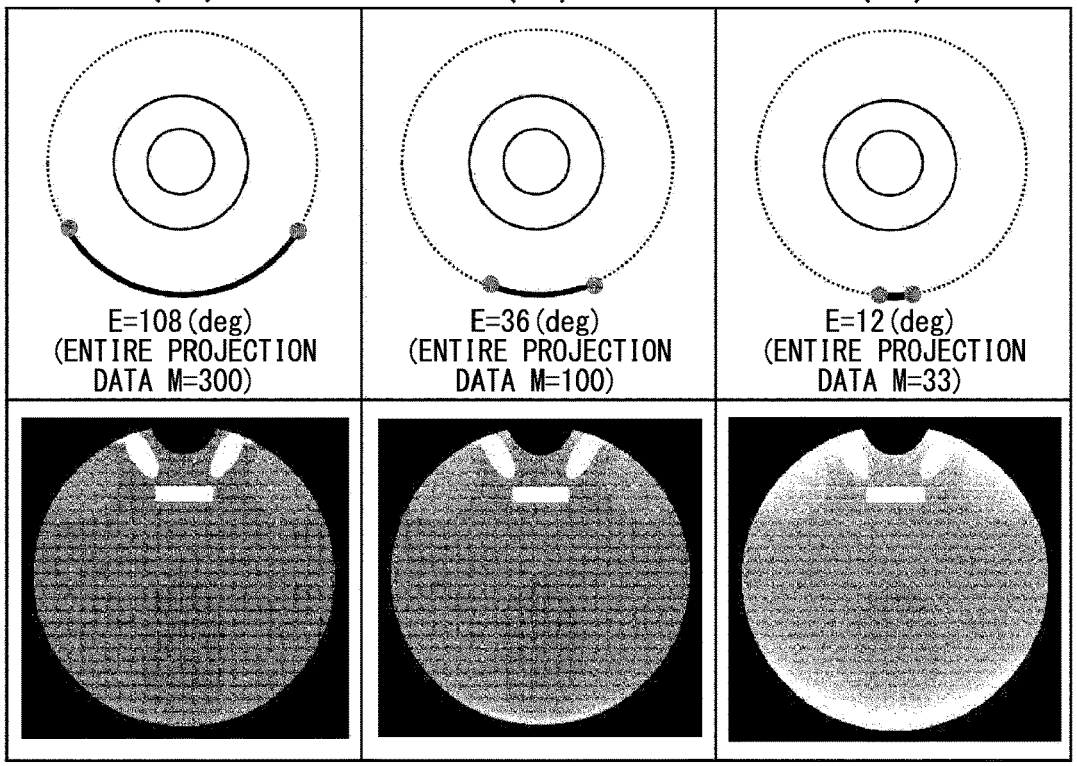
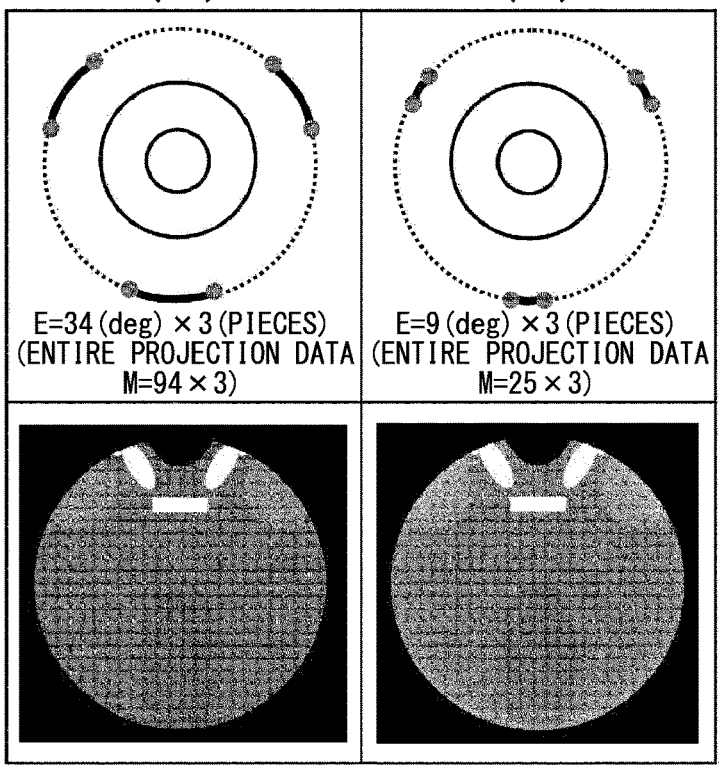
RECONSTRUCTED PICTURE BY METHOD OF PRESENT INVENTION WHEN CHANGING ANGULAR RANGE FOR MEASURING ENTIRE PROJECTION DATA
(a) E=108 (deg) (ENTIRE PROJECTION DATA M=300)
(b) E=36 (deg) (ENTIRE PROJECTION DATA M=100)
(c) E=12 (deg) (ENTIRE PROJECTION DATA M=33)
(d) E=34 (deg) × 3 (PIECES) (ENTIRE PROJECTION DATA M=94 × 3)
(e) E=9 (deg) × 3 (PIECES) (ENTIRE PROJECTION DATA M=25 × 3)
ALL DENSITY DISPLAY RANGE [1.0, 1.1]

FIG. 16A

ORIGINAL PICTURE

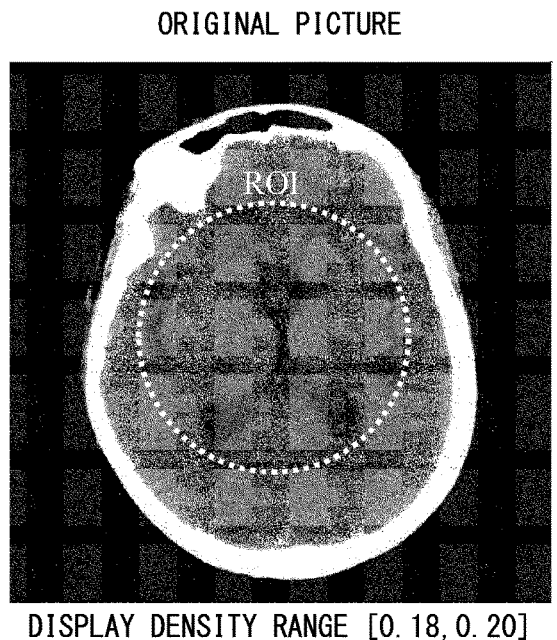

DISPLAY DENSITY RANGE [0.18, 0.20]

FIG. 16B

NO ENTIRE PROJECTION DTA
(LOCAL FBP METHOD)

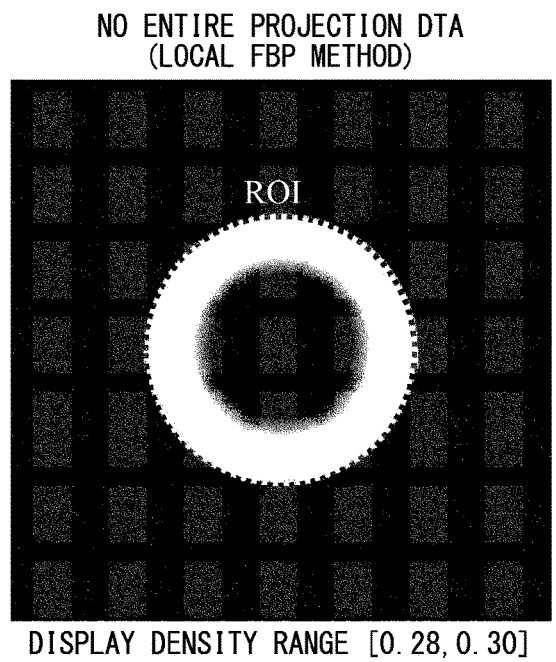

DISPLAY DENSITY RANGE [0.28, 0.30]

FIG. 16C

NO ENTIRE PROJECTION DATA
(SUCCESIVE APPROXIMATION PICTURE
RECONSTRUCTING METHOD)

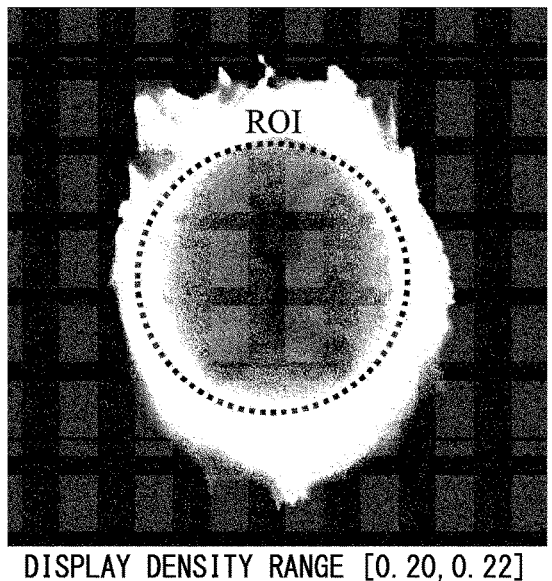

DISPLAY DENSITY RANGE [0.20, 0.22]

FIG. 16D

METHOD OF PRESENT INVENTION
WITH 1 ENTIRE PROJECTION DATA
(SUCCESIVE APPROXIMATION PICTURE
RECONSTRUCTING METHOD)

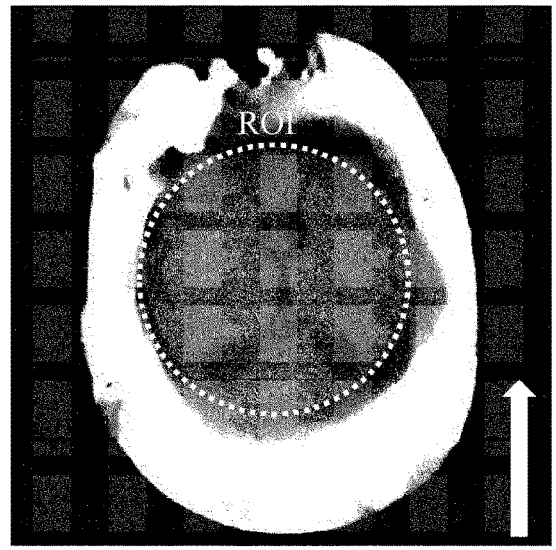

DISPLAY DENSITY RANGE [0.18, 0.20]  DIRECTION OF ENTIRE PROJECTION DATA

INTERIOR CT IMAGE GENERATION METHOD

TECHNICAL FIELD

The present invention relates to an image generation method of CT, for generating an image of distribution of physical quantities by measuring line integral values of the physical quantity distribution within an object or body, through data processing thereof, and in particular, it relates to the image generation method of interior CT.

BACKGROUND ART

Firstly, explanation will be given on a principle of interior CT (Computed Tomography). In the following, although there is assumed a case where quantum beams applied to CT measurement are X-rays, for making understanding of the explanation thereof easy: however, it is apparent that, for the person skilled in the art, it is also applicable, in the similar manner, to the others of all CTs applying the quantum beams therein. In the CT, from a viewpoint of purposes thereof, there can be supposed a situation that only an image of a small Region Of Interest (ROI) of an investigation is sufficient enough, such as, a heart or a breast, etc., for example, while the image of an outside of ROI is unnecessary. In the ordinary CT, even under such condition, as is shown in FIG. 1A, the projection data are measured by radiating not only the X-rays passing through the ROI, but also X-rays covering over the entire of an object. However, intuitively, because the projection data on a straight line not passing through the ROI has no information of that ROI, it is assumed to be unnecessary. Then, for abolishing such useless measurements, as is shown in FIG. 1B, CT of a method for generating the image of only the ROI by measuring the projection data while radiating only the X-rays passing through the ROI can be considered, and it is that, which is called "an interior CT". Such interior CT has following advantages, (1) reduction of exposure dose in the outside of ROI, (2) reduction of detectors and/or beam widths thereof, (3) enabling to photograph an image of a large object not within a field of view, etc. Also, in the CT apparatuses, such as micro (nano) CT, for enlarging and photographing a small field of view, there frequently occurs such a situation of the interior CT, where a sample overflows the field of view.

In this manner, within the interior CT, a problem of image reconstruction for generating the image from the projection data measured can be formulated, as below. As is shown in FIG. 2, it is assumed that measurement is made on all of the projection data passing through ROI Ω shown by solid lines, on the other hand no measurement is made on all of the projection data not passing through ROI Ω shown by a dotted line. And, how to reconstruct the image of the ROI Ω from such incomplete projection data, exactly or precisely, in a mathematical manner, is the problem of the image reconstruction in the interior CT.

On the other hand, in the conventional technology relating to the interior CT, first of all, in the Non-Patent Document [1], Natterer proved that a solution of the image reconstruction of interior CT cannot be determined, uniquely, and therefore that the mathematically exact image reconstruction is impossible. Then, various approximating solutions are studied for a long time; however they did not reach to a practical use because errors occur in the low frequency components of the image. For example, as the representative image reconstructing methods, studies are made on a method of conducting the image reconstruction by a filter correct reverse-projection (FBP: Filtered Backprojection) after extrapolating a lost portion of the projection data in each direction by a smooth function, and a method of applying a successive approximating method, for example, an algebraic reconstruction method (ART: Algebraic Reconstruction Technique) or a simultaneous iterative reconstruction method (SIRT: Simultaneous Iterative Reconstruction), etc. (Non-Patent Documents [2]~[4]).

FIG. 3A and FIG. 3B show examples of typical artifacts that occur in the interior CT. There occur, frequently, shading artifacts of distorting the low frequency components of the image and/or cupping artifacts of rising up the image values of peripheral portions of the ROI. For those previous studies, in 2007, finally, the mathematically exact image reconstructing method was found, and a new direction of the image reconstruction in the interior CT was established. Abstracting important key points of those exact solutions by words, it can be mentioned "The exact image reconstruction is impossible with only the projection data of the interior CT, but the mathematically exact image reconstruction can be made if there is a very small amount of prior information relating to the object".

Further, mentioning about the development of the exact solutions mentioned above herein, first of all, in the paper of Ye et al. of 2007 (Non-Patent Document [5]), in the paper of Kudo et al. of 2008 (Non-Patent Document [6]), and in the patent of Wang et al. of 2008 (Patent Document [1]), as is shown in FIG. 4A, if there is a prior information that the image values in an arbitrary small region B (a prior information region) within the ROI Ω is already known, it is proved that the exact image reconstruction of ROI Ω can be made. Next, in the paper of Yu et al. of 2009 (the Non-Patent Document [7]) and the patent of Wang et al. of 2014 (Patent Document [2]), as is shown in FIG. 4B if the image values are piecewise constant in an entire of the ROI Ω (being constructed by a finite number of pieces of regions each having a completely constant value), it is proved that the exact image reconstruction of the ROI Ω is possible. Further, in the paper of Yang et al. of 2010 (Non-Patent Document [8]), by expanding the method of Yu et al., as is shown in FIG. 4B, it is proved that the exact image reconstruction is possible if the image values are piecewise polynomial (being constructed by a finite number of regions each having changes that can be expressed by polynomials of finite degree). Lastly, in the patent application (PCT application) of Kudo et al., now pending, and in the paper of Kudo et al. (Non-Patent Document [9]), succeeding to reduce greatly the prior information that is necessary in the methods of Yu et al., Wang et al., and Yang et al., it is proved that the exact image reconstruction of ROI Ω is possible if the image values are piecewise constant or piecewise polynomial in the arbitrary small region B (the prior information region) within the ROI Ω.

In addition to the above, in Non-Patent Document [10] is shown the image reconstructing method having a FBP type structure, being called a FBP method of Katsevich, in Non-Patent Document [11], it is shown that the filter correct projection data in the FBP method of Katsevich has a symmetry, and in Non-Patent Document [12], it is shown that there are two (2) greatly different principles in the phase CT.

PRIOR ART DOCUMENTS

Patent Documents(s)

Patent Document 1: U.S. Pat. No. 7,697,658
Patent Document 2: U.S. Pat. No. 8,811,700

NON-PATENT DOCUMENT(S)

Non-patent Document 1: Natterer F: The Mathematics of Computerized Tomography. Wiley, 1986

Non-patent Document 2: Ogawa K, Nakajima M, Yuta S: A reconstruction algorithm from truncated projections. IEEE Transactions on Medical Imaging 3: 34-40, 1984

Non-patent Document 3: Ohnesorge B, Flohr T, Schwarz K, Heiken J P, Bae K T: Efficient correction for CT image artifacts caused by objects extending outside the scan field of view. Medical Physics 27: 39-46, 2000

Non-patent Document 4: Ohyama N, Shiraishi A, Honda T, Tsujiuchi J: Analysis and improvement in region-of-interest tomography. Applied Optics 23: 4105-4110, 1984

Non-patent Document 5: Ye Y, Yu H, Wei Y, Wang G: A general local reconstruction approach based on a truncated Hilbert transform. International Journal of Biomedical Imaging 2007: Article ID 63634, 2007

Non-patent Document 6: Kudo H, Courdurier M, Noo F, Defrise M: Tiny a priori knowledge solves the interior problem in computed tomography. Physics in Medicine and Biology 53: 2207-2231, 2008

Non-patent Document 7: Yu H, Wang G: Compressed sensing based interior tomography. Physics in Medicine and Biology 54: 2791-2805, 2009

Non-patent Document 8: Yang J, Yu H, Jiang M, Wang G: High order total variation minimization for interior tomography. Inverse Problems, 26: Article ID 35013, 2010

Non-patent Document 9: Kudo H: Practical interior tomography. Proceedings of International Forum on Medical Imaging in Asia 2017, Paper No. 07-1-2, 2017

Non-patent Document 10: Katsevich A, Analysis of an exact inversion algorithm for spiral cone-beam. CT, Physics in Medicine and Biology 47: 2583-2598, 2002

Non-patent Document 11: Noo F, Defrise M, Clackdoyle R, Kudo H: Image reconstruction from fan-beam projections on less than a short scan. Physics in Medicine and Biology 47: 2525-2546, 2002

Non-patent Document 12: Momose A: Phase Contrast X-ray Imaging. Synchrotron radiation 10: 27 3-285, 1997

BRIEF SUMMARY OF THE INVENTION

Problem(s) to be Solved by the Invention

In all of the exact solutions mentioned above, for enabling the mathematically exact image reconstruction, there is necessity of such a prior information, for example, that the values relating to the object are already known, or that they are already known to be piecewise constant, or that they are already known to be piecewise polynomial, etc.

On the other hand, as a method for obtaining the prior information in an actual CT imaging can be considered various methods; such as, (1) assumption from the previous CT image of the same patient or the image, which is photographed by other modality, (2) assumption from the CT image, which is photographed at the same portion of other patient, (3) assumption from the image including the artifact, which is reconstructed by the approximation solution proposed by the patent application (PCT application) mentioned above, by a user, manually or through an image analysis thereof, etc. And, in such an imaging condition that those prior information can be obtained, it is possible to reconstruct the image, by means of the exact solution, at an accuracy much higher than that obtained by the conventional approximation solutions. However, such a condition or situation, where the prior information is already known in relation to the object, is not so often, then it is not too much to say that it lacks the generality thereof.

Then, the present invention has an object thereof to provide an interior CT image generation method which is more practical and more versatile and which makes it possible to reconstruct the image with a high accuracy through the exact solution, even in the case where there are problem in the conventional technologies mentioned above; i.e., even in the case where the prior information cannot be used.

Means for Solving the Problem(s)

For achieving the object mentioned above, according to the present invention, first of all, there is provided an image generation method of an interior CT, comprising the following steps: a step for obtaining interior CT projection data by measuring quantum beams passing through a region of interest (ROI) in an inside of photographing object in a geometrical system for CT measurement; a step for obtaining partial entire projection data by measuring quantum beam passing through an entire of said photographing object from a segment in an outside of said photographing object in said geometrical system for CT measurement; wherein further including a processing step for exactly reconstructing said ROI upon basis of said interior CT projection data obtained, and said partial entire projection data.

According to the present invention, in the image generation method of an interior CT described in the above, it is preferable that said segment is an odd number (1,3,5, . . . ) of pieces of segments including a plural number of points corresponding to a curved line surrounding said photographing object therein, further that said interior CT projection data obtaining step is conducted by a 360 degrees circular orbit fan beam, and said partial obtaining of the entire projection data is conducted by a fan beam from said segment included in a circular orbit of said 360 degrees circular orbit fan beam for obtaining said interior CT projection data, or that said interior CT projection data obtaining step is conducted by a fan beam short scan, said partial entire projection data obtaining is conducted by fan beam from said segment included in an arc orbit of said fan beam short scan for obtaining said interior CT projection data, or that said interior CT projection data obtaining step is conducted by a 180 degrees parallel beam scan, and said partial entire projection data obtaining is conducted by a parallel beam from said segment included in an orbit of said 180 degrees parallel short beam scan for obtaining said interior CT projection data.

Also, according to the present invention, in the image generation method of an interior CT described in the above, it is preferable that said segment is so set that at least one or more projection data is included in an angle thereof, further that said reconstruction processing step of ROI is executed by any one of an analytic image reconstructing method, a successive approximation image reconstructing method and a statistic image reconstructing method, or a combination of those, further that an aperture angle of quantum beams for obtaining said interior CT projection data and said partial entire projection data is controlled by using an active collimator, further that as said partial entire projection data a Scout-View scan projection data is used, or preferable that said partial entire projection data is obtained with using measurement of radiating other quantum beams having spatial resolution, which is lower than said interior CT projection data, and further that said interior CT projection data and said entire projection data measured by radiating a quantum beam on an object are line integrals of spatial distribution of physical quantities of at least any one of absorption, phase shift, scattering, diffraction and refraction, which are caused due to mutual interaction between quantum beam and an object, on a straight line, along which said quantum beams pass through.

Also, according to the present invention, for achieving the object mentioned above, there is provided an image generation method of an interior CT, comprising the following steps: a step for obtaining interior CT projection data including truncation therein, by measuring quantum beams passing through a region of interest (ROI) in an inside of photographing object in a geometrical system for CT measurement; a step for obtaining partial entire projection data, not including truncation therein, by measuring quantum beams passing through an entire of said photographing object from a segment in an outside of said photographing object in said geometrical system for CT measurement; and further including a processing step for exactly reconstructing said ROI upon basis of said interior CT projection data obtained, including the truncation therein, and said partial entire projection data not including the truncation therein.

Also, according to the present invention, in the image generation method of an interior CT described in the above, it is preferable that said reconstruction processing step of ROI is executed by any one of an analytic image reconstructing method, a successive approximation image reconstructing method and a statistic image reconstructing method, or a combination of those, or that inability of calculation of Hilbert transform in said interior CT projection data including said truncation therein is brought into ability of calculation by using said partial entire projection data not including said truncation therein, and thereby reconstructing said ROI.

Effect(s) of the Invention

According to the present invention mentioned above, there is achieved a superior effect of providing the interior CT image generation method which is more practical and more versatile and which makes it possible to reconstruct the image with a high accuracy through the exact solution, even in the case where there are problem in the conventional technologies mentioned above; i.e., even in the case where the prior information cannot be used.

BRIEF DESCRIPTION OF THE DRAWINGS

FIGS. 3A and 3B are views for showing an example of typical artifacts generated in the interior CT;

FIG. 5 is a view for explaining the method for achieving the mathematically exact image reconstruction of the inte-rior CT without using the prior information, i.e., the image reconstructing method of the present invention;

FIG. 15 is a view for showing a result of numerical simulation conducted for showing an effect of the present invention;

FIGS. 16A to 16D are views for showing a result of additional numerical simulation conducted for showing an effect of the present invention;

EMBODIMENT FOR CARRYING OUT THE INVENTION

Figure 1A:
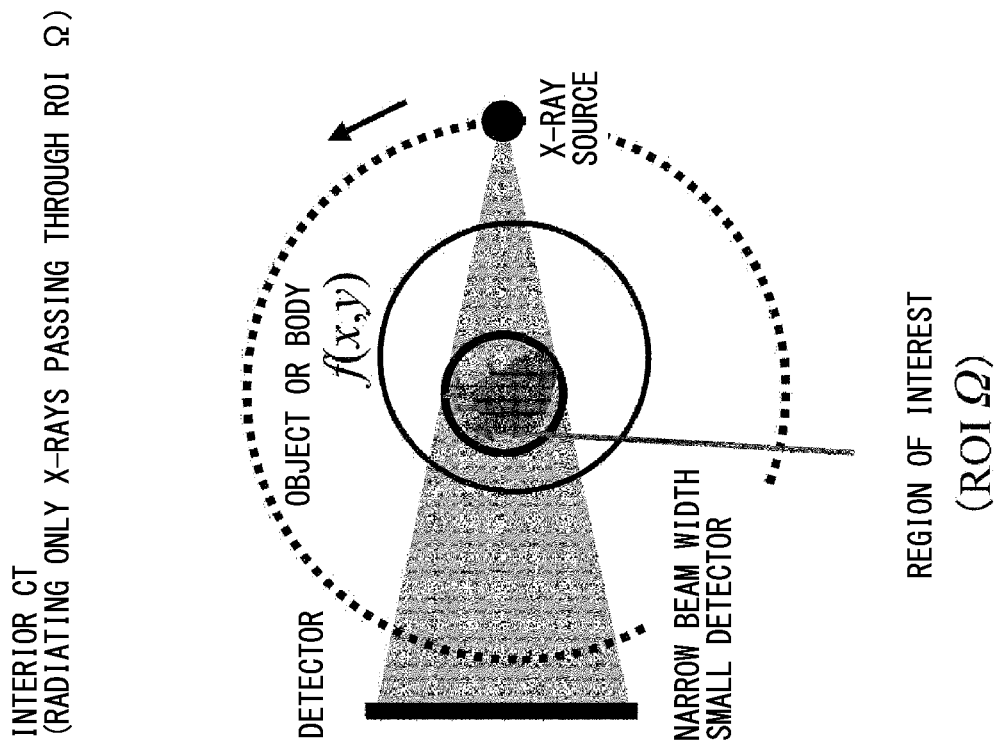
FIGS. 1A and 1B are views for explaining the interior CT relating to the present invention, comparing to an ordinary CT.
Figure 1B:
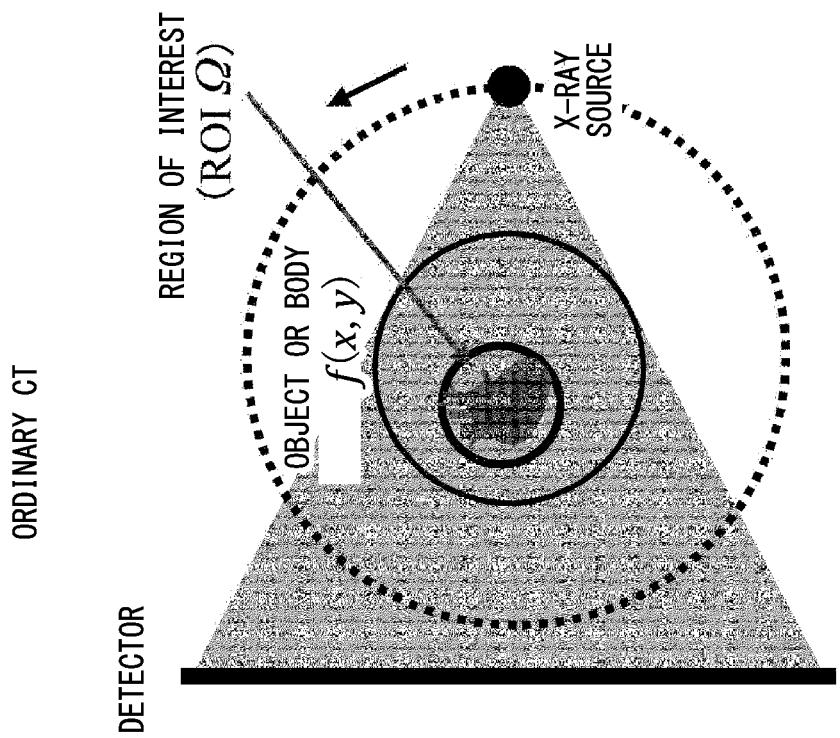
Figure 2:
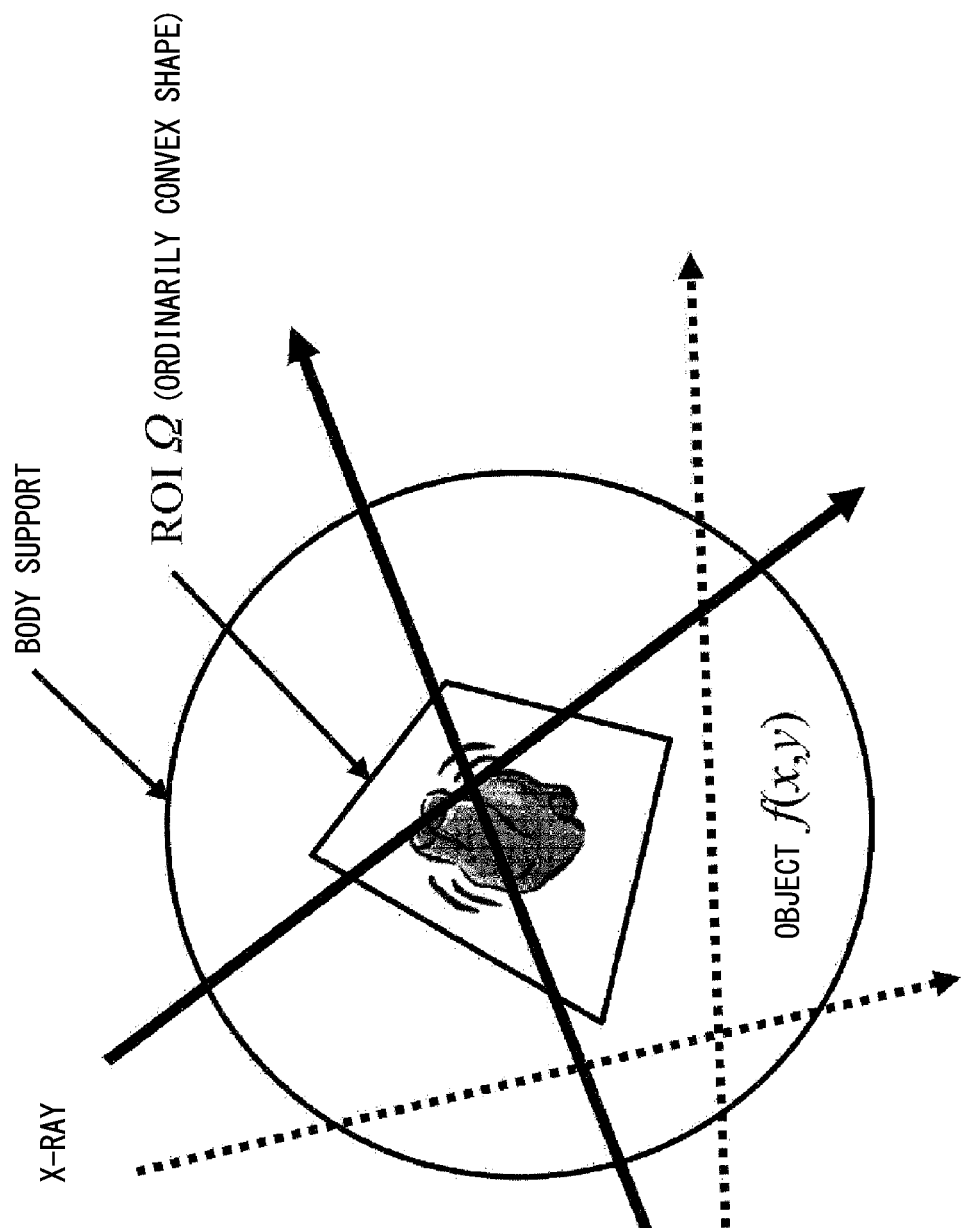
FIG. 2 is a view for explaining the definition of the image reconstruction problem in the interior CT.
Figure 4A:
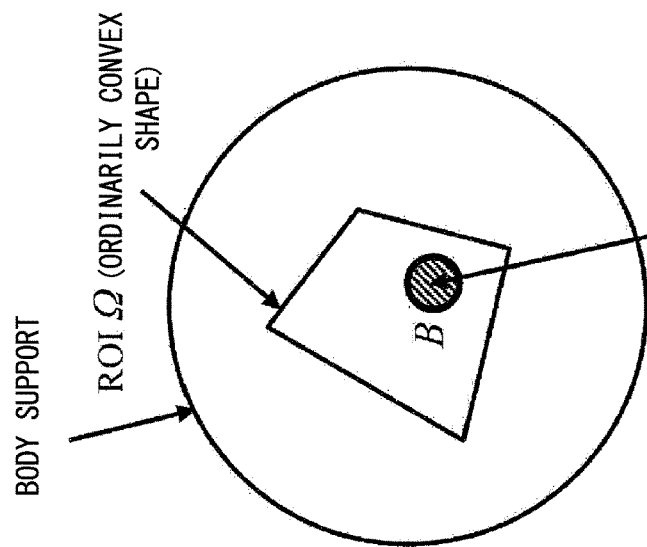
FIGS. 4A to 4C are views for explaining that exact image reconstruction of ROI can be made if the prior information of the image values is already known, or the image values are piecewise constant or piecewise polynomial.
Figure 4B:
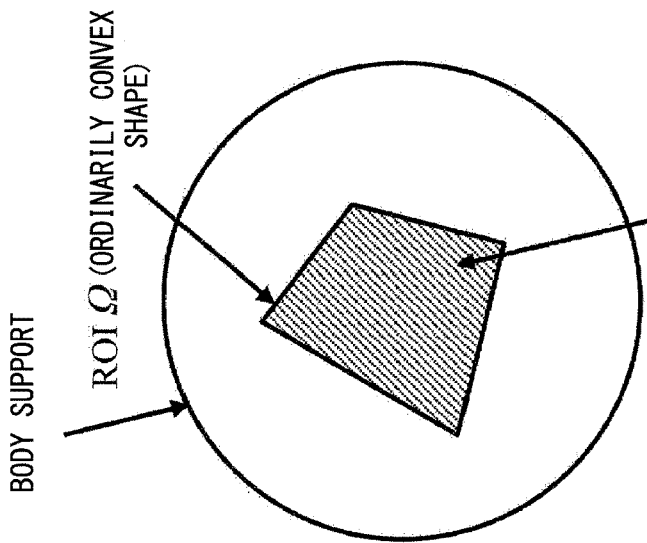
Figure 4C:
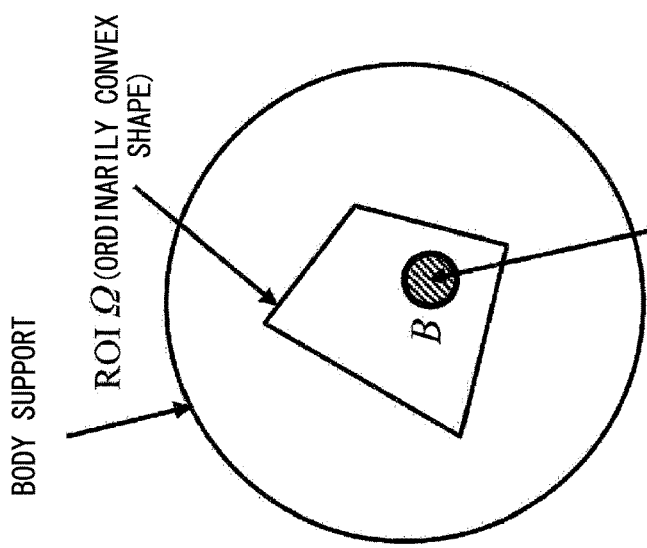

Hereinafter, although explanation will be given onto the details of an embodiment (s) of the present invention; however in advance thereto, an interior CT exact solution will be mentioned, which is proposed by the present inventors.

<Interior CT Exact Solution of Present Invention>

According to the present invention, there is provided a method for achieving the mathematically exact image reconstruction of the interior CT, without utilizing the prior information relating to the object, which is used in the conventional technologies mentioned above, and details thereof will be mentioned hereinafter.

For the purpose of enabling the exact reconstruction, with establishing the uniqueness of solution (i.e., a solution of the image reconstruction problem is determined uniquely), there is a necessity of any kind of additional information, in addition to the interior CT projection data. According to the conventional exact solution, as was mentioned previously, the solution can be determined uniquely by using the prior information relating to the object therein; however, according to the present invention, in the place of this, the projection data, which will not be measured, ordinarily, in the interior CT, i.e., an extra projection data not passing through the ROI Ω are measured, and this additional data is used therein. Thus, an important characteristic of the exact solution proposed lies in that the minimum extra projection data not passing through the ROI Ω is measured.

Further, the method mentioned above has a generality of being applicable into various kinds of geometric systems (in a track of an X-ray source and/or in a manner of outputting the X-rays from a light source, etc.) of the CT; however, hereinafter, explanation will be given on the principle about a fan beam CT, being practical at the most, in which the X-ray source moves on a circular orbit by 360 degrees.

As shown in FIG. 5(a), consideration is paid upon the condition or circumstances of the interior CT for measuring the projection data while radiating only the X-rays passing the ROI Ω, within the fan beam CT having the circular orbit of 360 degrees. Of course, only with an aid of the interior CT projection data, the mathematically exact reconstruction of the image of the ROI Ω is impossible, and as is shown in FIG. 5(b), as the additional information, the projection data of the entire are measured, while radiating the X-rays covering over the object as a whole from an arc segment E in a part of the circular orbit. This partial entire projection data (hereinafter, it will be also called only "an entire projection data") is added to the interior CT projection data, thereby enabling the exact reconstruction of the ROI Ω. In this case, the problems lie, roughly in the following two (2) aspects.

(1) How much degrees can be shorten the circular segment E for measuring the entire projection data (if a wide range E is necessary, it comes close to a non-interior CT, and then the advantages of the method proposed can be seemed to be small).

(2) If there are the entire projection data of the circular segment E, it is possible or not, mathematically, to prove that the exact image reconstruction of the ROI Ω can be made.

According to the present invention, with respect to the problem of (1) mentioned above, surprisingly, it can be proved that the E can be an arbitrary small arc segment.

Also, with respect to the problem of (2) mentioned above, although it cannot be proved by the image reconstruction method (the Non-patent Documents [5]-[9]), combining a differential reverse projection (DBP: Differentiated Back-projection) method, which is used as a tool for showing the uniqueness of the solution in the study of the interior CT exact solution, by using the prior information relating to the past object therein, and a truncation Hilbert transform; however, it can be proved by applying a new image reconstructing method introducing the truncation Hilbert transform into a filtering process in the FBP method (the details will be mentioned later). Herein, summarizing the uniqueness of the solution of the interior CT image reconstruction problem in the 360 degrees circular orbit fan beam, being apparent according to the present invention, it is as follows.

[Uniqueness of Solution]

In addition to the interior CT projection data, if there is an entire scan projection data (no truncations at the left side and the right side) of an arbitrary arc segment E (how much it is small does not matter), then the solution of the image reconstruction of the interior CT is unique.

About this new exact solution of the interior CT, in the following, at first, a result of uniqueness of the solution succeeding in proof thereof will be mentioned, and next the proof thereof will be shown.

<Uniqueness of Obtained Solution in Interior CT>

Herein, results of the uniqueness of the solution in the interior CT image reconstruction, being succeeded to prove upon basis of the new image reconstructing method of introducing the truncation Hilbert transform into the filtering process of the FBP method that will be explained later, will be mentioned, collectively. However, as a definition of a mark, a target image (i.e., the object) is presented by f(x,y) and the ROI by Ω.

(1) Regarding Uniqueness of Solution in Case of 360 Degrees Circular Orbit Fan Beam CT In the 360 degrees circular orbit fan beam CT shown in FIG. 5(a), consideration is paid upon the condition of the interior CT, where the projection data measurement is conducted while radiating only the X-rays passing through the ROI Ω. However, since the solution of the image reconstruction problem cannot be determined uniquely only with the interior CT projection data, then as shown in FIG. 5(b), the entire projection data are measured while radiating the X-rays covering over the object as a whole from an arbitrary small arc segment E on the circular orbit. In this instance, the following uniqueness of solution will be established.

[Uniqueness of Solution (360 Degrees Circular Orbit Fan Beam Scan)]

In addition to all of the projection data passing through the ROI Ω, if measuring the entire projection data from the arbitrary small arc segment E (how much it is small does not matter), then the image f(x,y) is determined uniquely in the ROI Ω, and then the exact reconstruction of Ω can be made.

However, the problem of this uniqueness lies in that, herein, because of being specialized to the 360 degrees circular orbit fan beam CT, it cannot be applied into the CT applying other geometric systems therein (for example, 180 degrees parallel beam scan, fan beam short scan, the fan beam scan with using non-circular orbit). Then, the uniqueness of the solution of the interior CT in the case of an arbitrary geometric system will be mentioned below.

(2) Uniqueness of Solution of Interior CT in Case of Arbitrary Geometric System

Then, the uniqueness of the solution in case of the 360 degrees circular orbit fan beam CT is generalized to be applicable to the projection data that are measured in the arbitrary geometric system.

Figure 6A:
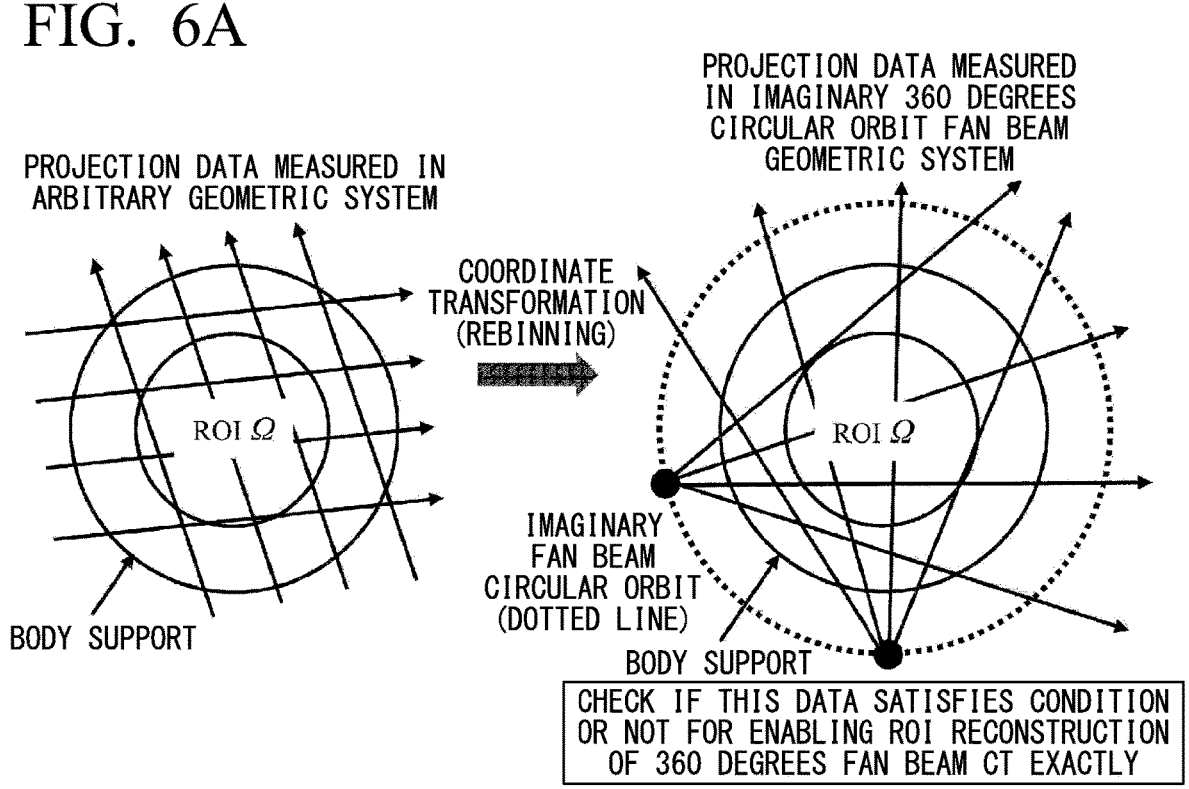
FIGS. 6A and 6B are views for explaining the way of thinking for generalizing the image reconstructing method of the present invention.
Figure 6B:
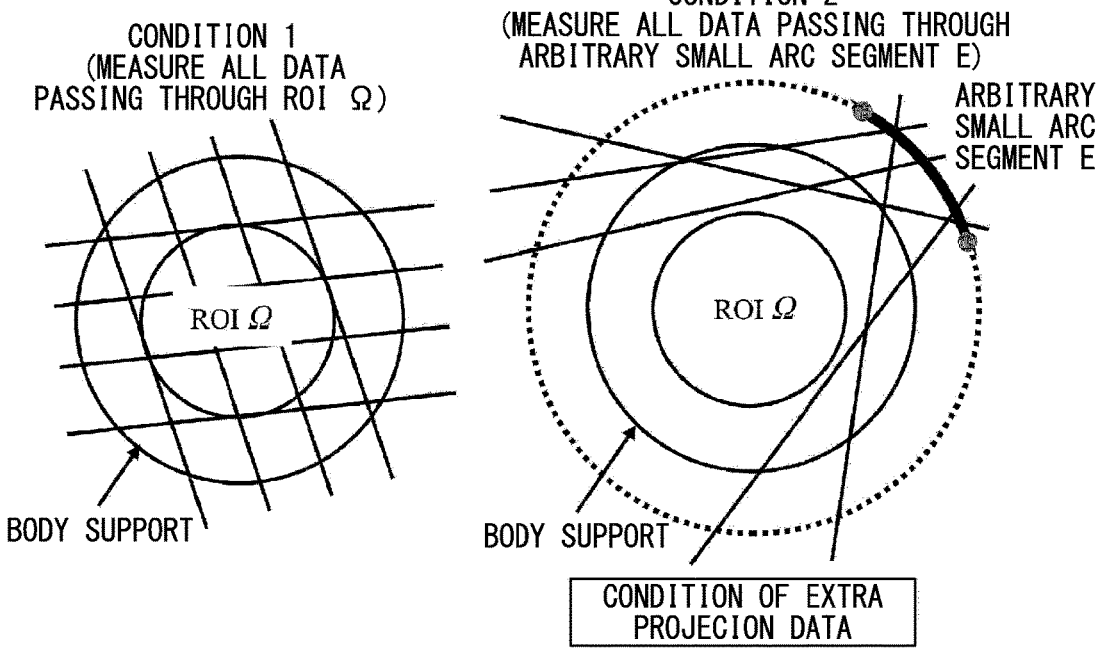

Firstly, upon basis of FIG. 6A and FIG. 6B, a way of thinking when generalizing will be mentioned. In the case of applying the arbitrary geometric system therein, and also in the case of the 360 degrees circular orbit fan beam CT, an aspect of measuring a set of line integral values on a straight line on the object is common with, and there is established a relationship of coordinate conversion (the coordinate conversion between the projection data is called by rebinning, in the field of CT) between the projection data of the both. Then, the projection data measured in the arbitrary geometric system are converted in the coordinates thereof, once, as is shown in FIG. 6A, into the projection data of an imaginary 360 degrees circular orbit fan beam CT, to check if that data satisfies or not the condition of the uniqueness in the case of the 360 degrees circular orbit fan beam CT, and then a decision is made that the uniqueness is established if it satisfies; i.e., this is the way of thinking as the fundamental thereof. Delivering the uniqueness of the applicable solution to the projection data measured in the arbitrary geometric system in this way of thinking, finally, the following conclusion can be obtained.

[Uniqueness of Solution (Arbitrary Geometric System)]

If the projection data are measured in such a manner that both of the following two (2) conditions are satisfied, the image f(x,y) is determined uniquely in the ROI $\Omega$, and then the exact reconstruction of $\Omega$ can be made.

(Condition 1) That all the projection data passing through the ROI $\Omega$ are measured (measurement condition of the interior CT).

(Condition 2) That the projection data (partial entire projection data) on all of straight lines passing through the arbitrary small arc segment E (corresponding to a circle including the object in an inside thereof) lying in an outside of the object are measured (i.e., the condition of the projection data to be measured in excess for determining the solution uniquely).

However, how much small the length of the small arc segment E is does not matter, and the position where it lies also does not matter (However, it is necessary that it must be the segment corresponding to a circle including the object in the inside thereof).

Meanings of the two (2) geometric conditions mentioned above are shown in FIG. 6B.

Further, three (3) cases will be mentioned below, where the uniqueness of the generalized solution mentioned above are effective. Any one of them is an example where capability of the exact reconstruction of the ROI $\Omega$ cannot be proved on the uniqueness of the solution in the case of the 360 degrees circular orbit fan beam CT.

(a) Case of 180 Degrees Parallel Beam Scan

Figure 7A:
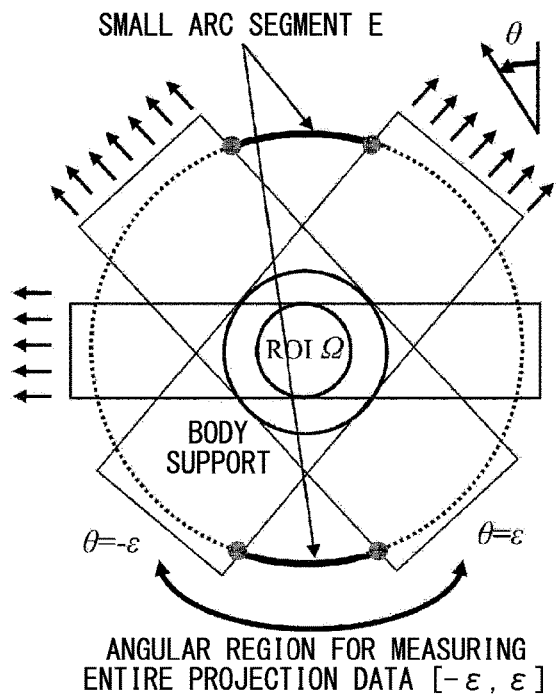
FIGS. 7A to 7C are views for explaining the cases of applying the image reconstructing method of the present invention mentioned above into a 180 degrees parallel beam, a fan beam short scan, and a polygonal orbit fan beam scan, respectively.

Consideration is paid upon the case of implementing the interior CT by applying the 180 degrees parallel beam scan therein, being most fundamental among the methods of collecting data of CT. The projection data is presented by p(r,$\theta$) (range of projection angle $-\pi/2 \leq \theta < \pi/2$) while assuming a moving radius is r and an angle is $\theta$. Now, it is assumed that the entire projection data (no truncation therein) can be measured in the angle range of $-\epsilon \leq \theta \leq \epsilon$ ($\epsilon$ is small angle), and that, in the others than that, only the interior projection data can be measured. In this instance, if taking position of the small arc segment E as is shown in FIG. 7A, it can be understood that it satisfies the uniqueness of the solution mentioned above, and then the solution of the ROI reconstruction is unique.

[Uniqueness of Solution (180 Degrees Parallel Beams)]

If measuring the entire projection data in the arbitrary small angular range E (how much small it is does not matter) in addition to the interior CT projection data in the angular range of $-\pi/2 \leq \theta < \pi/2$, then the image f(x,y) is determined uniquely in the ROI $\Omega$, and the exact reconstruction of $\Omega$ can be made.

However, this uniqueness can be interpreted as a limit when bringing the radius of the circular orbit to be infinite in the uniqueness of the solution in the case of the 360 degrees circular orbit fan beam CT, and in the 180 degrees parallel beams, there is also established the uniqueness of the solution, in the similar manner to the 360 degrees circular orbit fan beam CT. However, this result can be proved, firstly, by applying the uniqueness generalized to the arbitrary geometric system.

(b) Case of Fan Beam Short Scan

Figure 7B:
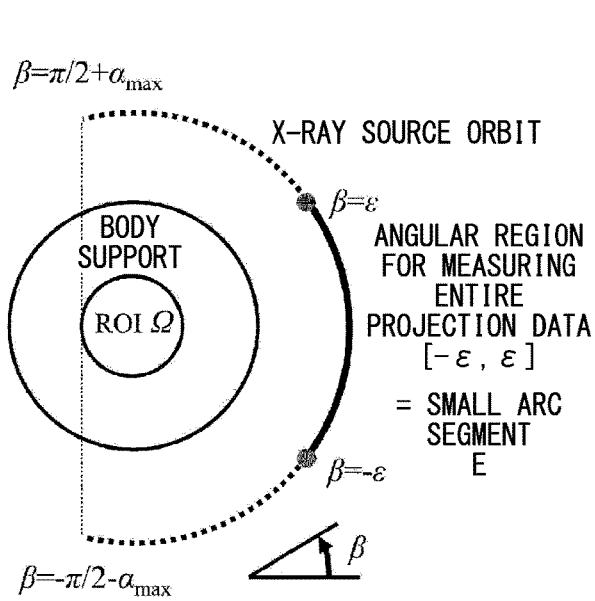

Consideration is paid on the case of the fan beam short scan shown in FIG. 7B. The fan beam data is presented by g($\mu$,$\beta$) while assuming the position of an X-ray source on the circular orbit is $\beta \in [-\pi/2-\alpha_{max}, \pi/2+\alpha_{max})$ ($\alpha_{max}$ is an over scan angle determined from the condition of short scan, the Non-patent Document [11]) and the coordinates on a straight line detector is u. Now, it is assumed that the entire projection data (no truncation therein) are measured in the angular range of $-\epsilon \leq \theta \leq \epsilon$ ($\epsilon$ is small angle), and that only the interior projection data can be measured in the others than that. In this instance, if taking position of the small arc segment E as is shown in FIG. 7B, it can be seen that it satisfies the condition of the uniqueness of the solution mentioned above, and then the solution of the ROI reconstruction is unique.

[Uniqueness of Solution (Fan Beam Short Scan)]

If measuring the entire projection data in the arbitrary small angular range E (how much it is small does not matter), in addition to the interior CT projection data in the angular range of $-\pi/2-\alpha_{max} \leq \beta < \pi/2+\alpha_{max}$, then the image f(x,y) is determined uniquely in the ROI $\Omega$, and the exact reconstruction of $\Omega$ can be made.

(c) Fan Beam Scan Using Polygonal Orbit

Figure 7C:
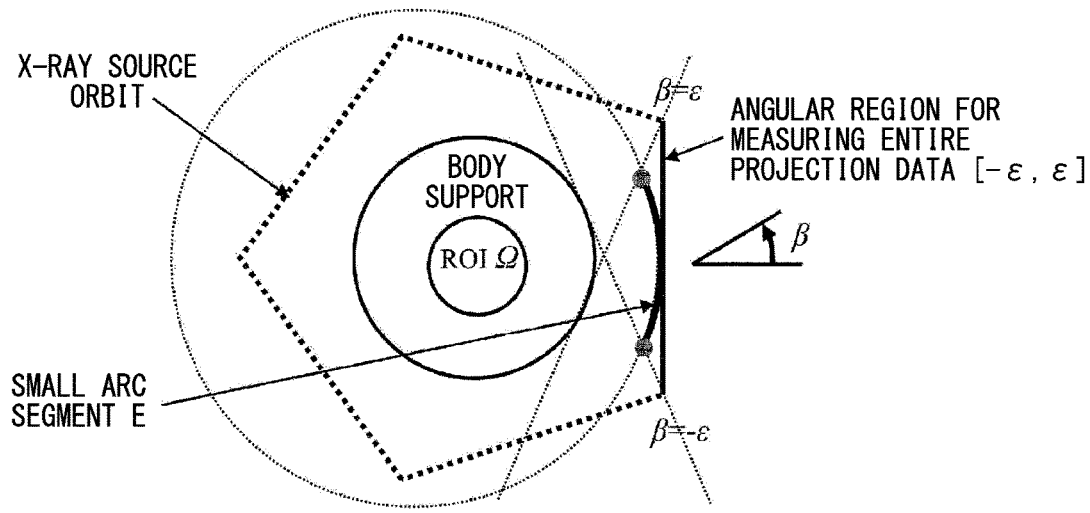

Consideration is paid on a fan beam scan using a regular pentagonal orbit shown in FIG. 7C. The fan beam data is presented by g($\mu$,$\beta$) while assuming the position of an X-ray source on the regular pentagonal orbit $\beta \in [-\pi, \pi)$ ($\beta$ is an angle of direction when seeing a point on the orbit from a center of the regular pentagon), and the coordinates on a straight line detector u. Now, it is assumed that the entire projection data (no truncation therein) are measured in the angular range of $-\epsilon \leq \beta \leq \epsilon$ ($\epsilon$ is small angle, and it is so determined that a side of the regular pentagonal orbit comes to E), and that only the interior projection data be measured in the others than that.

In this instance, if taking position of the small arc segment E as is shown in FIG. 7C, it can be understood that it satisfies the uniqueness of the solution mentioned above, and then the solution of the ROI reconstruction is unique.

[Uniqueness of Solution (Fan Beam Scan Using Polygonal Orbit)]

If measuring the entire projection data in the arbitrary small angular range E (how much small it is does not matter), in addition to the interior CT projection data in the angular range of $-\pi \leq \beta < \pi$, then the image f(x,y) is determined uniquely in the ROI $\Omega$, and the exact reconstruction of $\Omega$ can be made.

Of course, the three cases mentioned above are the fringes of showing that the uniqueness of the solutions with using the arbitrary geometrical system therein are effective, and it is apparent that, for the person skilled in the art, the range of the methods of collecting the data of CT is considerably wide, where the uniqueness of solution can be proved by the method of the present invention.

(3) Embodiments of Measurement

As was mentioned in the above, the feature of the present invention lies in an aspect of enabling the exact image reconstruction by measuring the entire projection data from the partial orbit E in addition to the ordinary interior CT projection data, and as the embodiments for achieving such the measurement, there can be considered various ones, depending on the hardware structure of each CT apparatus and on the imaging conditions thereof. Hereinafter, mentioning will be given on typical five (5) embodiments (a) to (e).

(a) Purely Conducting Two (2) Times of Measurement

The projection data measurement at a first time is conducted with using the X-rays covering over the object as a whole, from the small angular range E, and the measurement at a second time is conducted in such a manner that all of the interior CT projection data can be measured while radiating only the X-rays passing through the ROI.

(b) Using Scout-View Scan Projection Data for Positioning, into the Entire Projection Data In a micro (nano) CT apparatus and so on, for the purpose of positioning, i.e., putting the ROI to be seen or inspected in the view field, successively, before conducting the photographing, Scout-View scan is done with such a low resolution that the object as a whole can be entered into the view field. The projection data of this Scout-View scan can be used as the entire projection data of the partial orbit E.

(c) Apparatus with Using Plural Numbers of X-Ray Sources

In recent years, a medical use X-ray CT apparatus with using plural numbers of X-ray sources therein and/or micro (nano) CT apparatus are put into the practical use thereof. In those apparatuses, if setting up one of the plural numbers of the X-ray sources for measuring the entire projection data at low resolution, while the other X-ray source to photograph the ROI at high resolution, it is possible to use the low resolution projection data as the entire projection data of the partial orbit E.

(d) Method Using Active Collimator

With providing an active collimator, an angle of aperture of which can be changed actively, in front of the X-ray sources, and by controlling the angle of aperture to be large so that no truncation occurs in the partial orbit E, and to be small in the other than that, by controlling the angle of aperture to radiate only the X-rays passing through the ROI, thereby conducting the measurement of the projection data.

(e) Method for Estimating Entire Projection Data from Image Photographed Previously Through Calculation Thereof In the situation of being able to use the CT image, which is photographed previously on the same patient, or the CT image photographing the same portion of other patient, it is possible to estimate the data not yet measured by the truncation, from those images, among the projection data of the partial orbit E, through calculation thereof <Concrete Image Reconstructing Method>

As was mentioned above, it is possible to reconstruct the image correctly, if the projection data measured in any geometric system satisfies the condition of the uniqueness of the solution, even applying any method as the concrete image reconstructing method (as far as, if it is a mathematically correct method). Accordingly, there are an infinite number of choices or alternatives of the image reconstructing methods corresponding to the present invention. As the concrete examples, all of the following representative image reconstructing methods can be applied therein.

(1) Analytic Image Reconstructing Method

First of all, in case of the 360 degrees circular orbit fan beam CT, there can be used a new image reconstructing method introducing the truncation Hilbert transform in the filtering process in the FBP method, which is used for proving the uniqueness of the solution that will be mentioned later. In the case of the 360 degrees circular orbit fan beam CT, it is possible to use a direct reconstructing method expanding the image reconstructing method(s) mentioned above into each geometric system used for measuring, or to use the rebinning method of applying the image reconstructing method(s) mentioned above therein, after conducting coordinate conversion (i.e., the rebinning) on the 360 degrees circular orbit fan beam projection data once. Of course, if an analytic reconstructing method differing from those image reconstructing methods, which is used for the proof in the present invention, would be found in the future, it is also possible to replaced by that.

(2) Successive Approximation Image Reconstructing Method

When assuming image vectors arranging the pixel values of the image on a line and projection data vectors arranging the measured interior CT projection data on a line are x, b, respectively, the image reconstruction problem can be formulated into a problem of solution of a linear equation Ax=b. This linear equation can be solved with using a representative method of iteration in the field of the CT image reconstruction, such as, an ART method, a SIRT method, a simultaneous iterative ART (SART: Simultaneous Algebra Reconstruction Technique) method, and so on.

(3) Statistic Image Reconstructing Method

While defining an estimated projection data Ax, which can be calculated from the image x, and a distance (Ax,b) of actually measured projection data b, upon basis of the statistic characters of noises, and this distance is minimized with using a method of convex optimization. As the representative distances, there are, for example, a Weighted Least-Squares method (WLS), a emission type Poisson distribution logarithm likelihood, a transmission type Poisson distribution logarithm likelihood, etc. There are also existing a large number of iterative methods of convex optimization to be applied to the minimization of the distance.

Namely, if it is the measured interior CT data, the uniqueness of which is guaranteed, there is no concrete limit in selection of the image reconstructing methods (if being a mathematically correct method), therefore it means that any one may be alright.

<Proof of Uniqueness in Case of 360 Degrees Fan Beam CT>

Hereinafter, will be proved the uniqueness of the solution, being the fundamental of the present invention in the case of the 360 degrees fan beam CT, which seems to be highest in the possibility of practical use thereof. However, the method for generalizing into the arbitrary geometrical system is already explained. But the proof is conducted by showing a possible method enabling the exact image reconstruction, concretely, when satisfying the condition of the uniqueness, upon basis of the image reconstructing method having the FBP type structures, being called the Katsevich's FBP method, which was found in the Non-patent Document [10] in 2002.

(1) Fundamental Matters

Figure 8A:
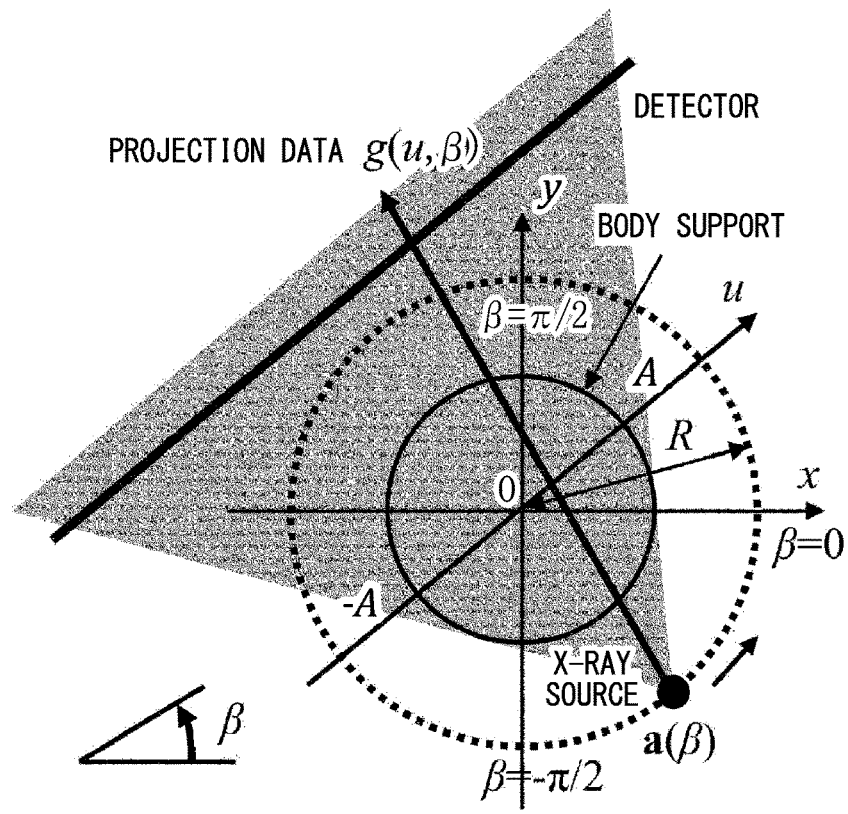
FIGS. 8A and 8B are views for showing the state of data collection of 360 degrees circle orbit fan beam in the cases of an ordinary CT and an interior CT.
Figure 8B:
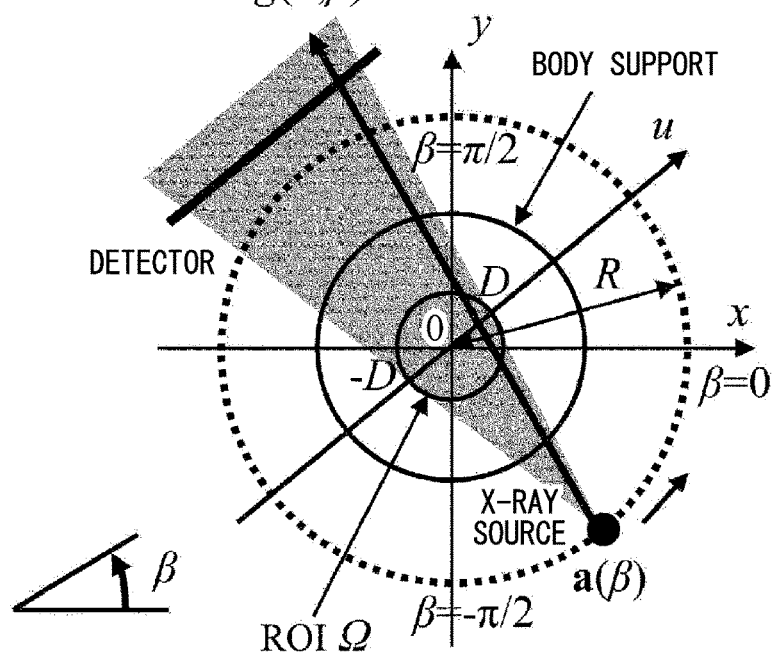

First of all, definition is made on setup of a problem to be considered in the proof, and also on terms and/or symbols to be used therein, and then explanation will be given on the image reconstructing method to be used in the proof, i.e., the Katsevich's FBP method. FIG. 8A and FIG. 8B show the states of the data collection of the 360 degrees circular orbit fan beam CT in cases of the ordinary CT and the interior CT. A body of the object of imaging is presented by f(x,y). And, consideration is paid on the situation where a support of the body (the region where the object exists) lies in a circle of radius a centering around an origin and the ROI Ω lies in a circle of radius d centering around the origin (however, a>d).

Also, the orbit on which the X-ray source moves is assumed to be a circle a $(\beta)=(R\cos\beta, R\sin\beta)$ ($\beta \in [-\pi,\pi)$) centering around the origin (however, ($\beta$) is a variable presenting the position of the X-ray source and R>a>d). And, the fan beam projection data measured from the position $\beta$ of each X-ray source are presented by the coordinate u on the straight line detector. Though the detector is provided in an outside of the object, but there is considered an imaginary detector passing through the origin in parallel with the actual detector, as is done often in the study of the image reconstruction, and the projection data are presented by using the coordinates u. Namely, the fan beam projection data is presented by g ($\mu,\beta$) in the form of two (2) variable function of ($\mu,\beta$). However, assumption of all the orbits of the X-ray source to be the circle centering around the origin is for the purpose of not bringing the description of mathematical expressions to be complex, and if the body support is included in an inside of the X-ray source orbit, and if it is in such geometrical disposition that the ROI $\Omega$ is included in an inside of the body support, it is mentioned that the following proof can be easily expanded with less changes, such as, by reading it differently with an interval of integration (this point will be mentioned again after the proof).

In the ordinary CT, since the X-rays are radiated in such a manner that it covers the body as a whole, the projection data are g ($\mu,\beta$) ($-A \le u \le A$, $\beta \in [-\pi, \pi)$) (but, $A=aR/(R^2-a^2)^{1/2}$); however, in the interior CT, since only the X-rays passing through the ROI $\Omega$ is radiated, then the measurement is made only in a range of g ($\mu,\beta$) ($-D \le u \le D$, $\beta \in [-\pi, \pi)$) being narrower in relation to the detector coordinates u (but, $D=dR/(R^2-d^2)^{1/2}$) (apparently D<A when d<a). Losing the left and the right sides of projection data g ($\mu, \beta$) in each direction is called the truncation, and it is a factor of bringing the image reconstruction of the interior CT to be difficult.

According to the present invention, there is used the FBP method, which was found by Katsevich in the Non-patent Document [10] in 2002, with targeting the ordinary non-interior CT. The detailed processing steps of this image reconstructing method will be shown collectively in the following.

[Step 1] Differentiation Filter

[Equation 1]

$$g^D(u, \beta) = \frac{R}{\sqrt{R^2+u^2}}\left(\frac{\partial}{\partial \beta} + \frac{R^2+u^2}{R}\frac{\partial}{\partial u}\right)g(u, \beta) \quad (1)$$

[Step 2] Hilbert transform filter

[Equation 2]

$$g^F(u', \beta) = -\frac{1}{\pi}p.v.\int_{-A}^{A}\frac{1}{u'-u}g^D(u, \beta)du \quad (2)$$

[Step 3] Back projection

[Equation 3]

$$f(x, y) = \frac{1}{4\pi} \int_{-\pi}^{\pi}\frac{1}{R-x\cos\beta-y\sin\beta}g^F(U(x, y), \beta)d\beta\left(U(x, y) = \frac{R(-x\sin\beta+y\cos\beta)}{R-x\cos\beta-y\sin\beta}\right) \quad (3)$$

However, p and v present Cauchy's principal values of integration, and an integral transform presented by the equation (2) is called, Hilbert Transform. In the ordinary FBP method, a filtering for correcting the blurring of the reconstructed image is conducted by one (1) time of convolution by means of a ramp filter, but the Katsevich's FBP method is different from, in an aspect that the ramp filter is divided into the differentiation and the Hilbert transform, wherein the differentiation is made in the Step 1 and the Hilbert transform is calculated in the Step 2. The reason of using such special FBP method in the proof will come to be clear in the following, but it is the purpose of utilizing the skillful characters of the Hilbert Transform.

(2) Proof of Uniqueness of Solution

The Katsevich's FBP method is the image reconstructing method assuming the ordinary non-interior CT therein. Then, consideration will be made on what kind of differences are there, when applying this image reconstructing method into the projection data of the non-interior CT or the interior CT, and where the calculation will be collapsed in the interior CT. Results thereof are shown in FIG. 9, in the form of table, collectively.

Figure 9:
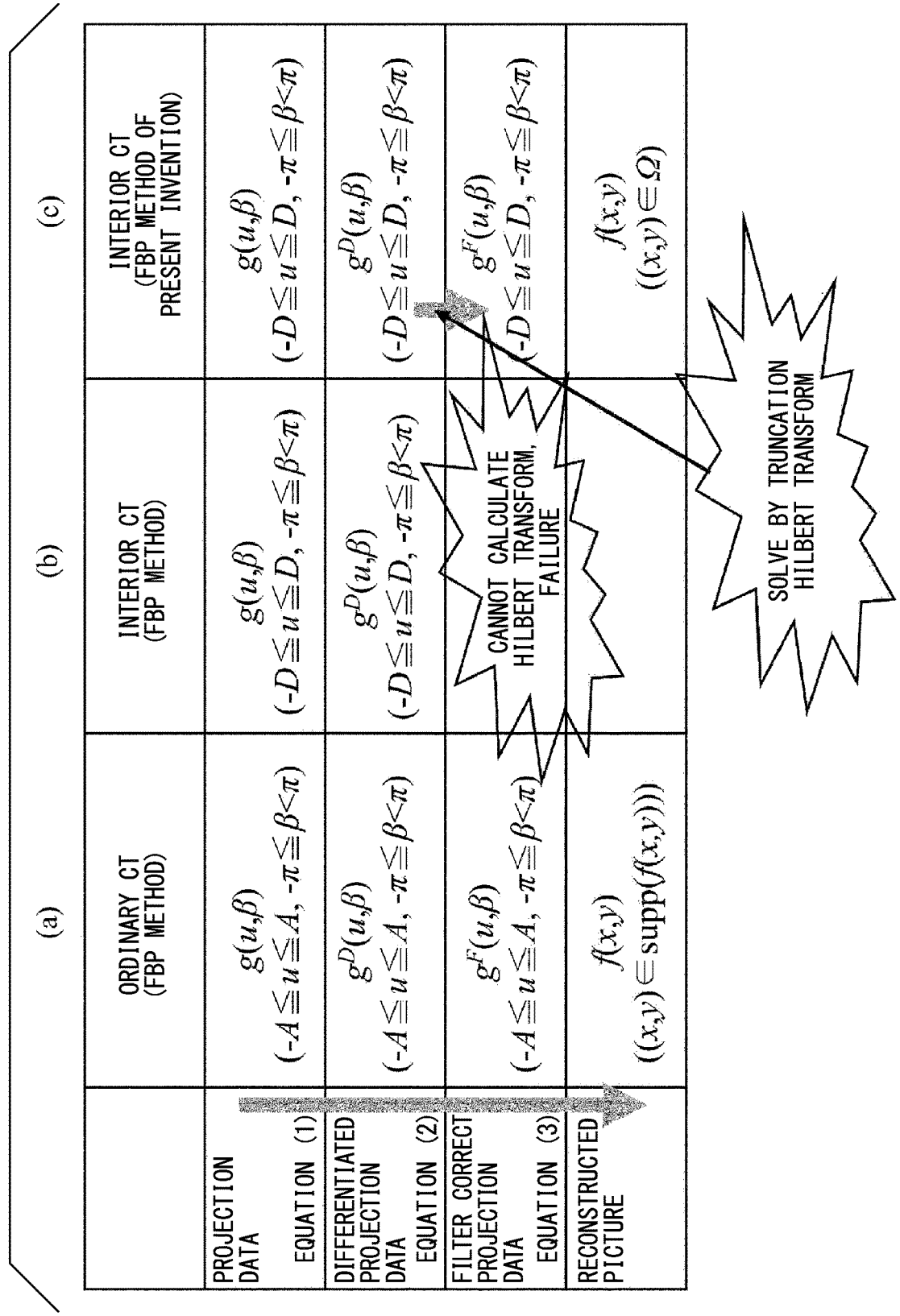
FIG. 9 is a view for showing a result of study made on differences and failures of calculation when applying the image reconstructing method upon projection data of the non-interior CT and the interior CT.

In the columns (a) and (b) in FIG. 9 are shown the regions where each function can calculate, when conducting the calculation by means of the equations (1) to (3) mentioned above, with paying attention to the facts that the differentiation is a local calculation which can be calculated by only neighborhood data, and that the integration can be calculated, firstly, only if there exist all the data of the integral region. Because the differentiation of the equation (1) is a local calculation, it can be calculated without any problem in the non-interior CT or the interior CT, in any case thereof. However, the Hilbert transform of the equation (2) can be calculated without any problem in the non-interior CT, in which $g(\mu,\beta)$ is measured in the range of $-A \le u \le A$; however, it cannot be calculated in the interior CT, in which the truncations are on the left and right sides of the projection data and $g(\mu,\beta)$ is measured only in the range of $-D \le u \le D$. Namely, in the interior CT, the calculation of the FBP method is collapsed at the position of the Hilbert transform, and it cannot be continued.

Then, according to the present invention, as will be mentioned below, it is shown that, if the entire projection data (no truncation therein) are measured in an small angular range $E=\{\beta| -\varepsilon \le \beta \le \varepsilon\}$ ($\varepsilon$ is small angle) of the X-ray source, the mathematically exact image reconstruction of the ROI $\Omega$ can be made by obtaining the projection data $g^F$ ($\mu,\beta$) ($-D \le u \le D$, $\beta \in [-\pi, \pi)$), on which a filter correction is made by correctly calculating the position of that uncalculatable Hilbert transform mentioned above, and by conducting a back projection thereon.

In the (c) column in FIG. 9 is shown the region of each function that can be calculated by that new method. However, hereinafter, for the purpose of simplification thereof, the angular range E of the X-ray source where the entire projection data can be measured is set at $-\varepsilon \le \beta \le \varepsilon$, but the proof is completely same to that even if E is in other angular range. Now, it is proved. First of all, mentioning will be given on important two (2) characters of the Hilbert transform to be applied in the proof. A first one is the character of being called "symmetry of the filter correct projection data". The $g^F(\mu,\beta)$, upon which the differentiation filter and the Hilbert transform filter act by the equations (1) and (2) (in other words, the projection data, upon which the ramp filter is acted) has the symmetry shown in the following lemma 1.

[Lemma 1]

Figure 10A:
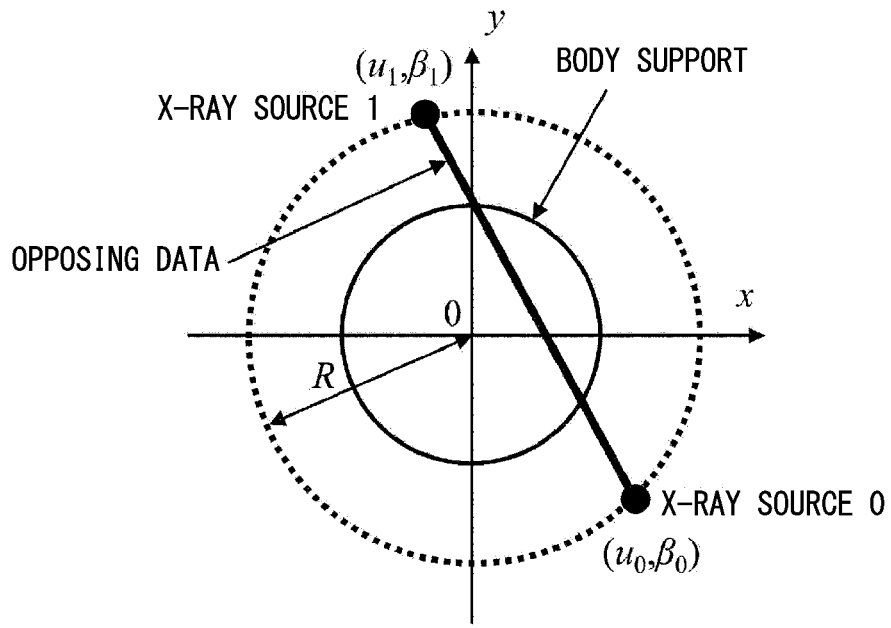
FIGS. 10A and 10B are views for explaining a symmetry of filter correct projection data in Katsevich's FBP method, regarding to projection data coordinates at 2 opposing positions.

As is shown in FIG. 10A, assuming ($\mu_0,\beta_0$) and ($\mu_1, \beta_1$) are the projection data coordinates of two (2) positions opposing to each other, then the filter correct projection data $g^F(\mu,\beta)$ has the following symmetry.

[Equation 4]

$$g^F(\mu_0,\beta_0)=g^F(\mu_1,\beta_1) \qquad (4)$$

Figure 10B:
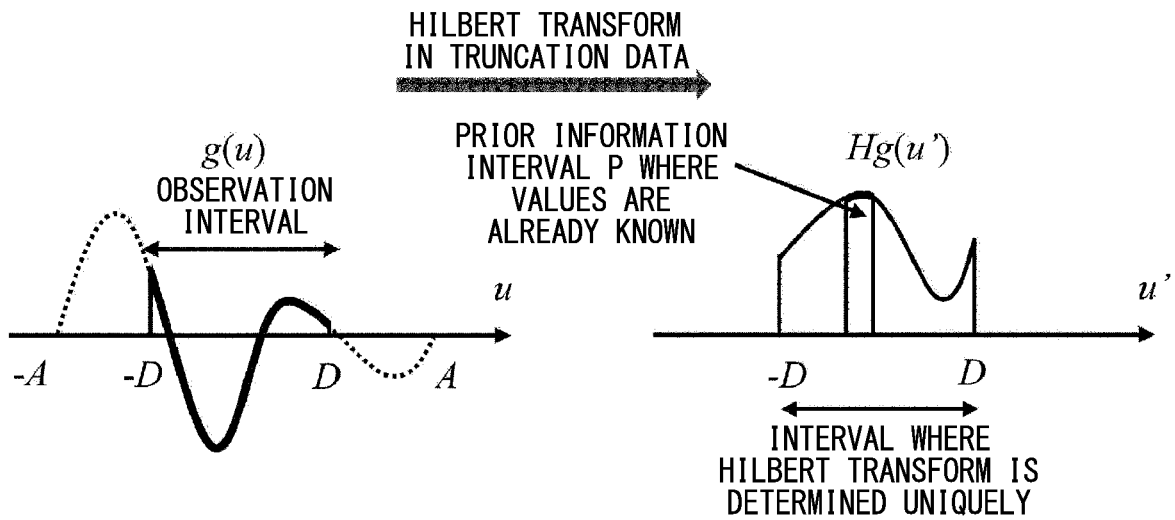

Regarding the proof of the lemma 1, please refer to the Non-patent Document [11] of Noo et al. It is self-evident that the symmetry as shown by the equation (4) is established on the original projection data $g(\mu,\beta)$ measured, but this surprising character lies in that it can be also established regarding to the projection data $g^F(\mu, \beta)$ after the filtering in the Katsevich's FBP method. Next, the second character is that, which is called "possibility of calculation of the truncation Hilbert transform". Now, as is shown in FIG. 10B, there is a function of $g(\mu)$, which is observed only in a partial interval [−D,D] included in the support (the interval where the function is not zero) [−A,A], and consideration is paid upon the situation of wishing to calculate the Hilbert transform that is defined by that following equation.

[Equation 5]

$$g^H(u') \equiv Hg(u') = -\frac{1}{\pi}p.v.\int_{-A}^{A}\frac{1}{u'-u}g(u)du \qquad (5)$$

Of course, for ordinarily calculating the equation (5), $g(\mu)$ of the entire interval [−A,A] are necessary; however this character lies in that the Hg ($\mu'$) can be determined uniquely and calculated correctly in [−D,D] as a whole, even if being observed only in the partial interval [−D,D], but as the result of conducting the Hilbert transform thereon, if Hg($\mu'$) is already known in the arbitrary small interval u' ∈ P ⊂ [−D,D] (prior information interval) included in [−D,D]. That is summarized in the following lemma 2.

[Lemma 2]

If the function $g(\mu)$ having the support of [−A,A] is observed only in [−D, D] ⊂ [−A, A], and also if the Hilbert transform Hg($\mu'$) of $g(\mu)$ is already known in the arbitrary small interval u'∈P⊂ [−D,D] included in [−D,D], then Hg($\mu'$) can be determined uniquely in the observation interval [−D,D] as a whole, and can be calculated correctly from the observation data $g(\mu)$ (−D≤$\mu$≤D).

Regarding the proof of the lemma 2 and the concrete calculating method thereof, please refer to the Non-Patent Document [6] of Kudo et al. In the Non-Patent Document [6], the truncation Hilbert transform mentioned above is calculated by means of a method of iterative method, with using the prior information, being called a convex projection method, as the condition of constraint. As other calculating method of non-iteration, it can be also calculated by means of calculation of pseudo inverse matrix calculation with using the singular value decomposition of the matrix. By using the two (2) characters mentioned above, there can be shown the fact, i.e., being the purpose thereof, that "if the entire projection data (no truncation therein) are measured in the small angular range −ε≤β≤ε(ε is small angle), it is possible to obtain the filter correct projection data $g^F(\mu, \beta)$ (−D≤$\mu$≤D, β∈[−n,n)) uniquely, by calculating the uncalculatable position of the Hilbert transform mentioned above, correctly". The proof is conducted by the process of two (2) steps, which will be mentioned below. First of all, in the first step, the proof is made on the case where the angular range −ε≤β≤ε of the entire projection data is sufficiently large (ε is large), and next, in the second step is made a proof that the angular range of the entire projection data −ε≤β≤ε can be made as small as possible.

(a) First Step (in the Case where the Angular Range E of the Entire Projection Data is Large)

Figure 11:
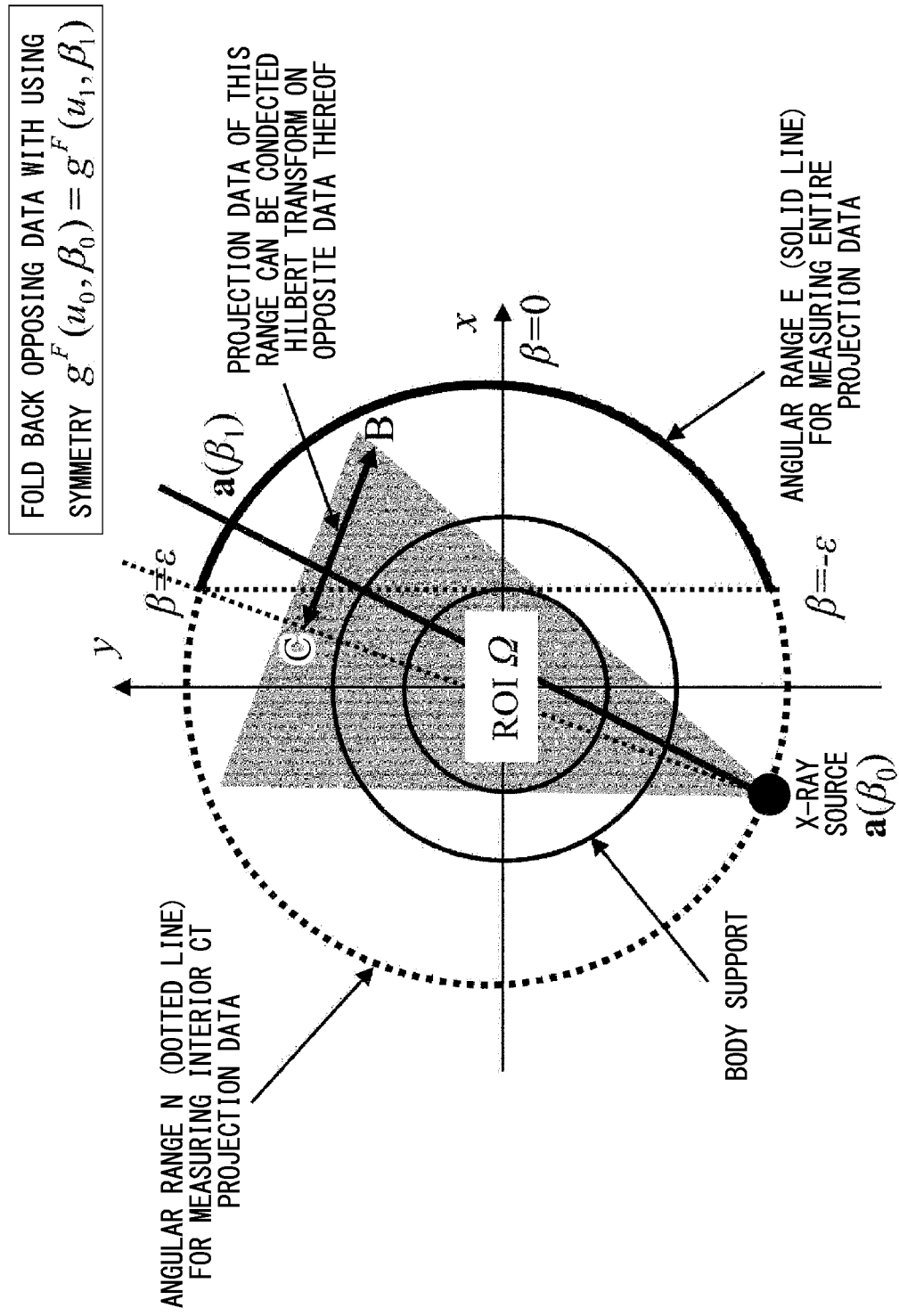
FIG. 11 is a view for explaining the state when an angular range E of the entire projection data is large.

First of all, consideration is paid upon such a situation as shown in FIG. 11. In FIG. 11, the solid line presents the angular range E=}β|−ε≤β_ε} of the X-ray source orbit where the entire projection data $g(\mu, \beta)$ (−A≤$\mu$≤A) are measured, and the dotted line presents the angular range N=[−π, π)E of the orbit where only the interior CT projection data $g(\mu,\beta)$ (−D≤$\mu$≤D) are measured (however, the small angle c is determined from an arc segment, which the vertical line contacting on the boundary of the ROI Ω cuts off from the orbit). In this case, since g ($\mu, \beta$) of the angular range E is the entire projection data, it is possible to calculate $g^F$ ($\mu, \beta$) (−A≤$\mu$≤A), on which the differentiation and the Hilbert transform can be made by the equations (1) and (2) without any problem. However, in the angular range N where only the interior CT projection data is measured, it falls into situation that the differentiation can be calculated but the Hilbert transform cannot be calculated. On the contrary to this, when applying the lemma 1 and the lemma 2 by combining them ably, $g^F(\mu,\beta)$ (−D≤$\mu$≤D) can be calculated correctly by the next steps.

The following Step 1 and Step 2 are conducted upon the truncation projection data of each $\beta_0$∈N.

[Step 1] (Constructing the Hilbert Transform Prior Information)

By folding $g^F(\mu,\beta)$, the differentiation and the Hilbert transform of which are calculated in the region of B-C in FIG. 11 facing to $\beta_0$, back to p side to be collected, and also by applying the symmetry of the lemma 1, it is possible to establish the prior information of $g^F(\mu,\beta_0)$ (Namely, it is possible to construct the situation that $g^F(\mu,\beta_0)$ is already known in the small interval $\mu$∈P⊂ [−D,D]).

[Step 2] (Truncation Hilbert Transform)

With using $g^F(\mu,\beta_0)$ ($\mu$∈ P) constructed in the Step 1 as the prior information, the filter correct data $g^F(\mu,\beta_0)$ (−D≤$\mu$≤D) is calculated from the data $g^D(\mu,\beta_0)$ (−D≤$\mu$≤D), on which the differentiation filter is conducted by the method of the truncation Hilbert transform of the lemma 2.

In the case of setting up that the angular range E of the entire projection data is large, as shown in FIG. 11, the prior information section P (not an empty set) can be constructed for all β∈ N, and with this method can be calculated $g^F(\mu,\beta)$ (−D≤$\mu$≤D), correctly, for all β∈ N. Accordingly, by conducting back projecting on the filter corrected projection data $g^F(\mu,\beta)$ (−D ≤$\mu$≤D, β∈ [−π, π)) by the equation (3), the mathematically exact image reconstruction of the ROI Ω can be made.

(b) Second Sep (in Case where the Angular Range E of the Entire Projection Data is an Arbitrary Small Arc Segment)

With only the proof of the first step, it is impossible to show the fact that the angular range of the entire projection data, which was mentioned in the conclusion of the uniqueness of the solution, can be the arbitrary small arc segment E. For showing this far strong result, device is necessary one more. The manner of how to make the proof on that fact is shown in FIG. 12.

A fundamental idea lies in repeating an operation for enlarging the angular range of the X-ray source orbit, in which the Hilbert transform can be made with using the opposing data mentioned in the first step, by a plural number of times.

Figure 12:
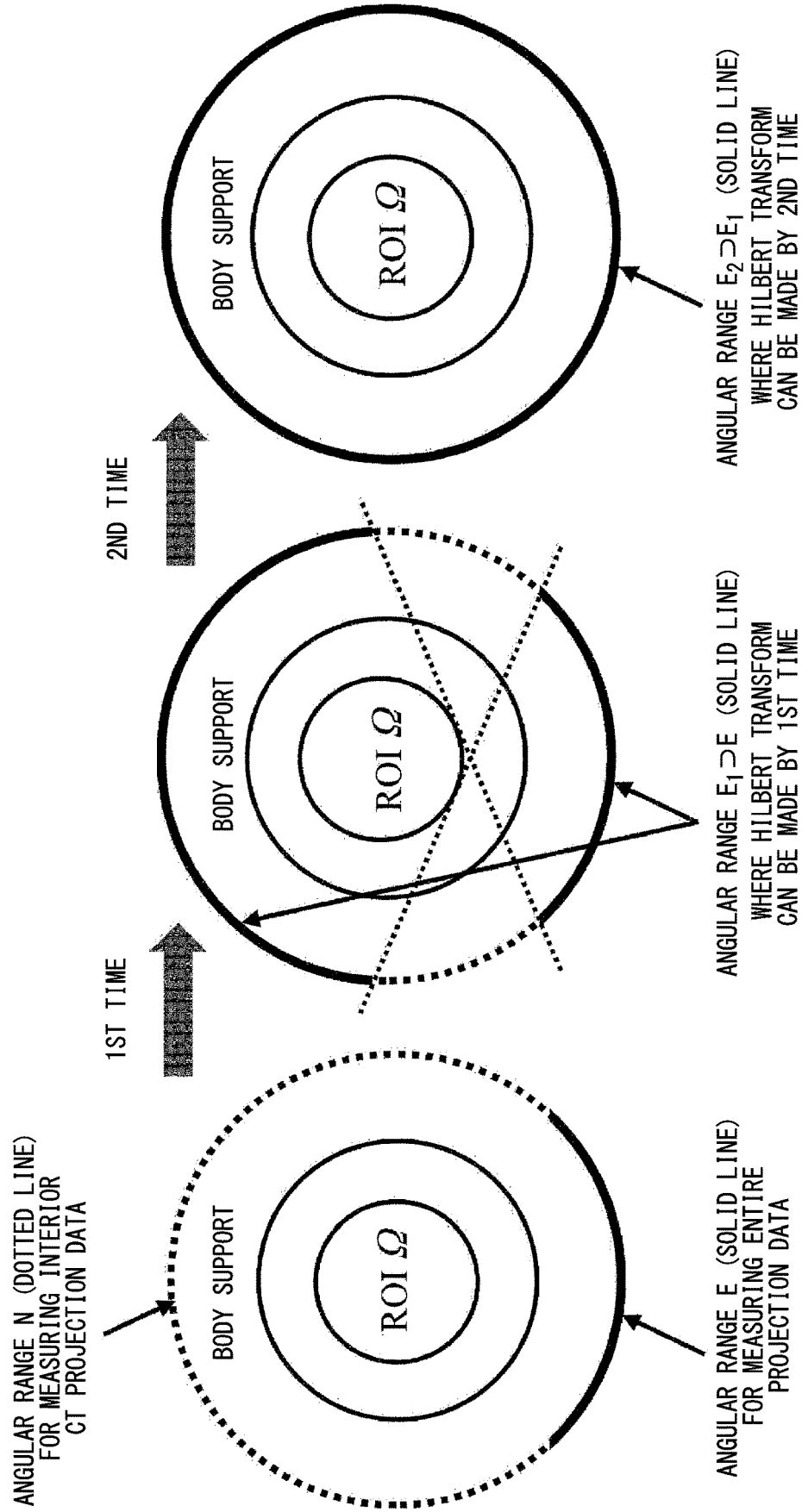
FIG. 12 is a view for explaining the state when the angular range E of the entire projection data is an arbitrary small arc segment.

In the example shown in FIG. 12, starting from the angular range E where the Hilbert transform can be made inherently, and after conducting the operation of the first step by one (1) time, the angular range $E_1$ where the Hilbert transform can be made is enlarged to the drawing at the center thereof, and further conducting the operation of the first step, one more time, then the Hilbert transform can be made for all $\beta \in [-n,n)$. In this example, two (2) times of the operation are sufficient enough, but in general, as far as E is not the empty set, it is possible to prove, geometrically, that an infinite number of times of the operations can bring the 360 degrees angular range $\beta \in [-\pi, \pi)$ to reach the condition of enabling the Hilbert transform therein, necessarily. Therefore, because the filter correct projection data $g^F(\mu,\beta)$ ($-D \leq \mu \leq D$, $\beta \in [-n, n)$) sufficient enough to generate the image of the ROI Q can be calculated through the back projection of the equation (3), then it is possible to reconstruct the ROI Ω exactly and correctly.

Summarizing the conclusion relating to the uniqueness of the solutions obtained finally, it comes to be as follows.

[Theorem]

In the 360 degrees circular orbit fan beam CT, being the setting up shown in FIG. 8B (the X-ray source orbit is a circle having radius R centering around an origin, the body support is a circle having radius a centering around an origin, and the ROI Ω is a circle having radius d centering around an origin), if measuring the entire projection data from the arbitrary small arc segment E (how much small it is does not matter) in addition to all of the projection data passing through the ROI Ω, then the image f(x,y) is determined uniquely at ROI Ω, and the exact reconstruction of Ω can be made.

In the theorem mentioned above, considerations are paid on the cases where the X-ray source orbit, the body support and the ROI Ω are circles centering around the origins, so as not to bring the equations appearing in the proof complex too much; however, it is easy to make proof on the following two (2) systems by expanding this proof. Concretely saying, although the region of integration and so on in the image reconstructing method to be applied into the proof changes, much or less, but the essence and the steps of the proof is still same too.

[System 1]

Figure 13A:
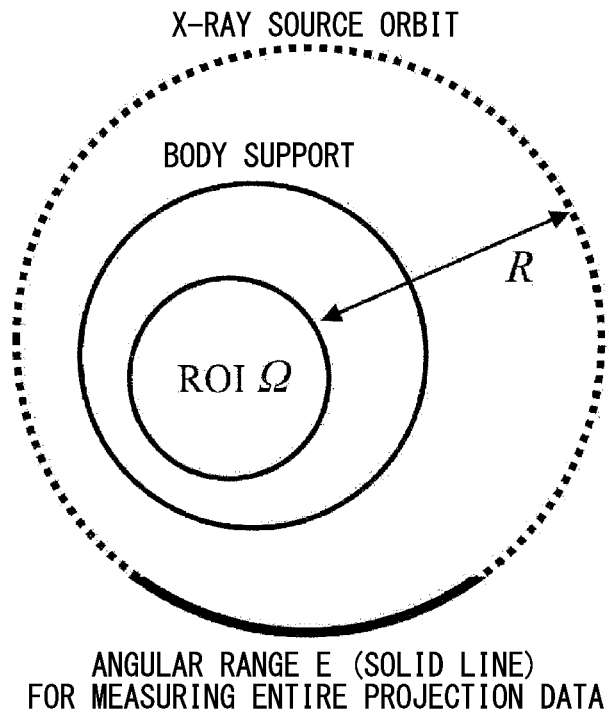
FIGS. 13A and 13B are views for explaining settings of a system 1 and a system 2, considering the general cases therein where the X-ray source orbit, the body support and the ROI $\Omega$ are not the circle centering around an origin thereof.

In the 360 degrees circular orbit fan beam CT of the setting up shown in FIG. 13A (the X-ray source orbit is a circle of radius R, the body support is an arbitrary circle included in an inside of the circular orbit, and the ROI Ω is an arbitrary circle included in an inside of the body support), by measuring the entire projection data from the arbitrary small arc segment E (how much small it is does not matter) in addition to all of the projection data passing through the ROI Ω, the image f (x,y) is determined uniquely at ROI Ω, and the exact reconstruction of Ω can be made.

[System 2]

Figure 13B:
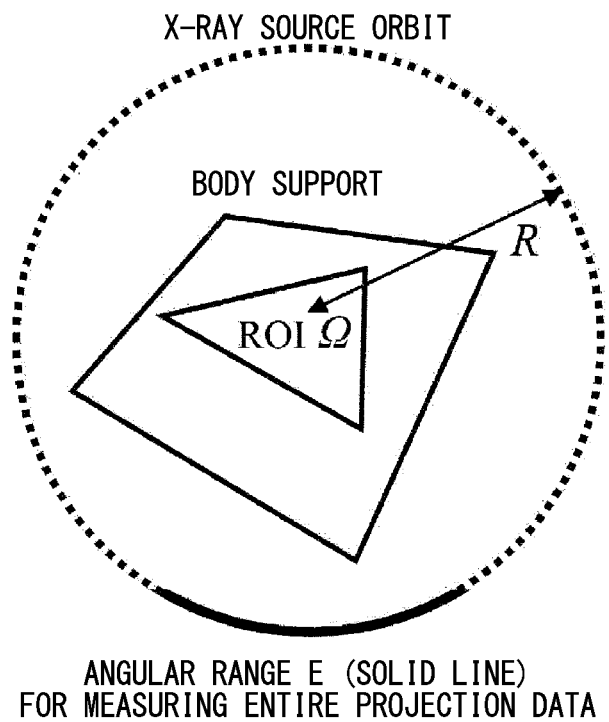

In the 360 degrees circular orbit fan beam CT of the setting up shown in FIG. 13B (the X-ray source orbit is a circle of radius R, the body support is an arbitrary convex shaped region included in the inside of the circular orbit, and the ROI Ω is an arbitrary convex shaped region included in the inside of the body support), by measuring the entire projection data from the arbitrary small arc segment E (how much small it is does not matter) in addition to all of the projection data passing through the ROI Ω, the image f (x,y) is determined uniquely in ROI Ω, and the exact reconstruction of Ω can be made.

<Result of Simulation Observation>

Figure 14:
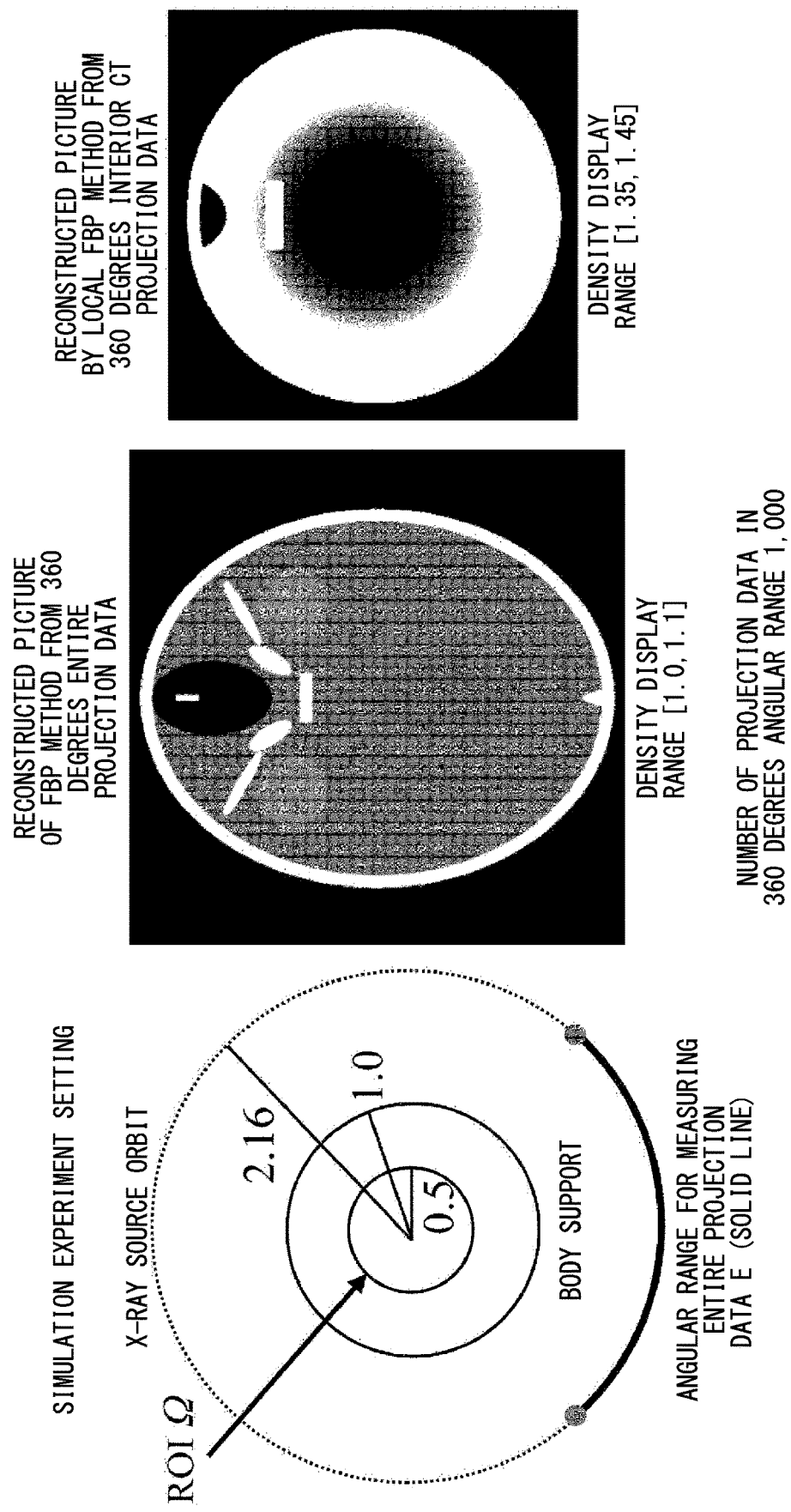
FIG. 14 is a view for showing a result of numerical simulation conducted for showing an effect of the present invention.

FIGS. 14 and 15 show the result of numerical simulation experiment, which is conducted for showing the effectiveness of the present invention. In the experiment, the image reconstruction is conducted with using numerical phantoms simulating the CT image of a head of the human body. The number of the fan beam projection data (the view number) per 360 degrees is 1,000, and the image reconstruction is conducted on 3 patterns of M=300, M=100, M=33. However, herein, M=300 corresponds to the case where the angular range of E is 108 degrees, M=100 corresponds to the case where the angular range of E is 36 degrees, and M=33 corresponds to the case where the angular range of E is 12 degrees, respectively. Also, in addition to the case where the segment mentioned above is 1 piece, the experiment is also conducted on the case where the segments mentioned above are 3 pieces. In the case where the segments E are the 3 pieces of segments, setting up is made that M=94 ×3 pieces (34 degrees ×3 pieces) and M=2 5×3 pieces (9 degrees×3 pieces). FIG. 15(a), FIG. 15(b) and FIG. 15(c) show the reconstruction images in the case where the small arc segment E is 1 piece, and FIG. 15(d) and FIG. 15(e) are the reconstruction images in the case where the small arc segments E are 3 pieces, respectively.

The method applied in the image reconstruction is a exact solution for enabling the image reconstruction exactly by introducing the truncation Hilbert transform into the filtering process in the Katsevich's FBP method, which is used in proof of the uniqueness of the solution. Also, for the purpose of comparison, the experiments are conducted on the ordinary FBP method of the case where all of the projection data are the entire projection data, and the local FBP method, which is used often at the most in the case where all of the projection data are the interior CT projection data (reconstructing the image through the FBP method after making extrapolation on the lost portion of the projection data by a smoothing function).

As apparent from those figures, with the local FBP method, the cupping artifact occurs, strongly, rising up the image values in the peripheral portion of the ROI, on the contrary to that, with the method of the present invention, in which the number of piece of the segment E is 1 piece, the image reconstruction of ROI can be made almost completely regarding M=300 and M=100. However, regarding the case of M=33, where the angular range of E is small comparing to the M=300 and M=100, the artifacts of low frequency components increase a little bit, but comparing to the local FBP method, it can be seen that the errors occur less far away. Also, a tendency of achieving the image reconstruction having less artifacts can be seen in the case where the number of pieces of the segment E is 3, comparing to the case of applying E of the equal angular range by 1 piece thereof.

<Result of Additional Simulation Experiment>

FIG. 16A, FIG. 16B, FIG. 16C and FIG. 16D show the results of the additional numerical simulation experiment, which is conducted for showing the effectiveness of the present invention. In the experiment, the image reconstruction is made by applying CT actual image of the head of the human body, which is measured by the medical use X-ray CT apparatus, as the numerical phantoms. With assuming the 180 degrees parallel beam scan therein, the projection data number (view number) per 180 degrees is set to 800, and the image reconstruction is made in the most difficult case, where the segment E mentioned above is 1 piece and the projection data number M within the small arc segment E for measuring the entire projection data is M=1 (that is the number of the entire projection data items is only (1)). However, herein, M=1 corresponds to the case where the angular range of E is 0.225 degree. FIG. 16A shows an original image, FIG. 16B shows the image reconstructed through the local FBP method in the case where no entire projection data is used, FIG. 16C shows the image reconstructed through successive approximation method in the case where no entire projection data is used, and FIG. 16D shows the image reconstructed through the method of the present invention with using 1 piece of the entire projection data, respectively.

The method used in the image reconstruction is the successive approximation image reconstructing method mentioned in the column [0059]. In more details, assuming the projection data vector, arranging the pixel values of the image on one line, and the projection data vector, arranging the interior CT projection data measured and 1 piece of the entire projection data on one line, are x and b, respectively, the image reconstruction problem is formulated into a problem of solving a linear equation Ax=b, and this linear equation is solved by using ART method, being the representative method of iteration in the field of the reconstruction of CT image. However, in an actual implementation, regularization (the Non-Patent Document [7]) is treated weakly by total variation (TV), for suppressing an influence of increase of the calculation errors as the iteration progresses.

As apparent from this figure, in the ordinary interior CT using no entire projection data therein, the artifact is generated, strongly, due to the cupping effect of rising the pixel values in peripheral portion of the ROI and direct current component shift of the image through the local FBP or the successive approximation method; therefore, the image quality is deteriorated in such a manner that the structures in the brain cannot be seen; however on the contrary thereto, with the method of the present invention of measuring only 1 set of the entire projection data from the 1 piece of segment E to be used complementarily, the image reconstruction can be made on ROI almost completely. In the preset experiment, there can be assumed the case where the entire projection data has no error and/or noise, at all; however, in the case that the measuring accuracy of the entire projection data is high, as can be seen in the result of the present experiment, by complementing only 1 set of the entire projection data measured from 1 piece of segment E, the conclusion can be made that the artifact generating in the interior CT can be removed almost completely.

<Method Using Arc Segment for Measuring Plural Numbers of Entire Projection Data>

In the discussion given heretofore, consideration is paid only the case where the arc segment E for measuring the entire projection data is single, in order to determine the solution of the image reconstruction problem uniquely. Also in this case, although it is possible to prove mathematically that the segment E for measuring the entire projection data can be made as small as possible, by repeating the operation of expanding the angular range where the Hilbert transform can be made, which is conducted in the second step of the proof mentioned above, by plural numbers of times, successively; however, if the number of times of the operations of this second step is large, it is deeply concerned that the image reconstruction comes to be complex, and the stability (the solution can be easily determined, uniquely, but not be influenced, sensitively, by the noises and/or the calculation errors) is deteriorated; and it is confirmed that the artifact increases if E is small, also in the simulation experiment mentioned above.

Then, for easing this problem, as the method for making the segment E for measuring the entire projection data sufficiently small, even by one (1) time of the operation of enlarging the angular range where the Hilbert transform can be made (only the first step of the proof), there is developed a method of dividing E into the plural numbers of small arc segments to be set up.

Figure 17A:
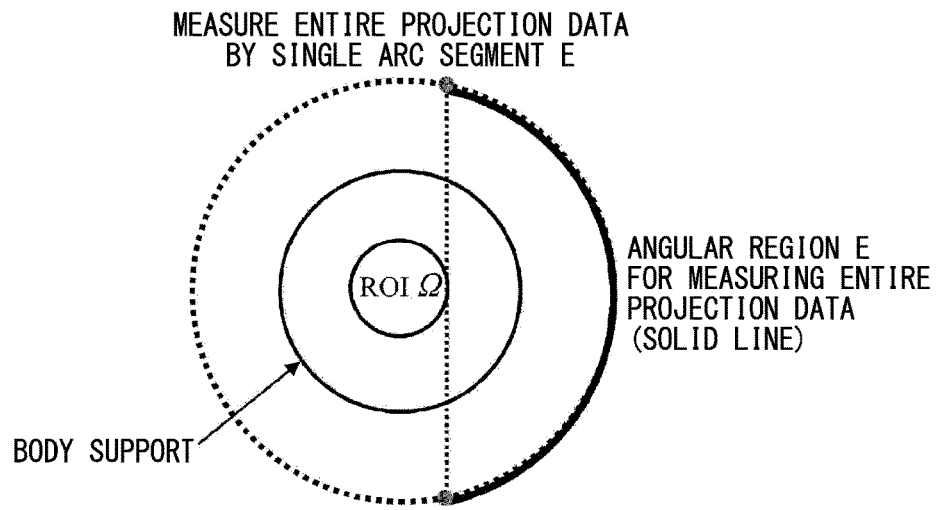
FIGS. 17A to 17C are views for showing the principle of dividing the segment for measuring the entire projection data into plural numbers of small arc segment to be set up.
Figure 17B:
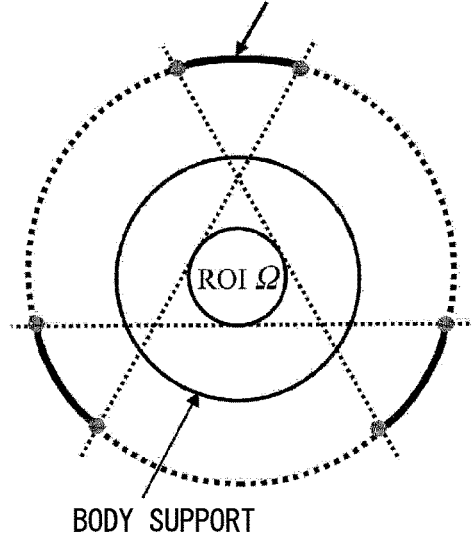
Figure 17C:
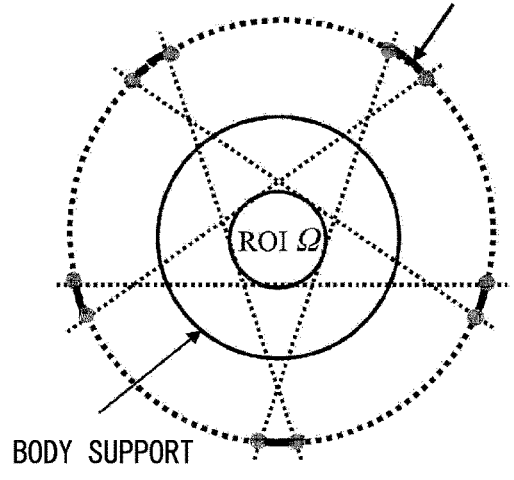

FIG. 17A, FIG. 17B and FIG. 17C show the principle of the present method. In the case where the arc segment E for measuring the entire projection data is single, for settling by only one time of the operation of enlarging the angular range where the Hilbert transform can be made, (as mentioned in the proof) as shown in FIG. 17A, it is necessary to make E considerably large. On the contrary to this, as shown in FIGS. 17B and C, if dividing the angular range E for measuring the entire projection data into the small arc segments positioned at an equal distance therebetween by an odd number n of pieces (n=3, 5, . . . ) and setting up them, it is far easy to build up the situation of existing the prior information interval u EP of knowing apart from the opposing data for the interior CT projection data β∈N in any direction, then it is possible to reduce the angular range of E small, greatly, in total (it is apparent from the comparison of FIG. 17A and the FIGS. 17B and C). Namely, if it is possible to position the segment E for measuring the entire projection data, dividedly, the image reconstruction can be achieved stably much more, with E much smaller.

<Expansion to Phase X-Ray CT>

Heretofore, the explanation was given, mainly, by assuming an absorption CT for imaging the distribution of X-ray absorption coefficient of an inside of the body or the object; however, in the recent years is advanced the practical application of the phase CT for imaging the distribution of phase shift amount therein. It is shown that the uniqueness of the solution mentioned in the present invention can be established also in case of such the phase CT, in completely similar manner. Hereinafter, the reasons thereof will be mentioned briefly.

In the phase CT, there exist the following two (2) principles, greatly differing from each other (the Non-Patent Document [12]).

(1) Method by Bonse-Hart Type Interferometer with Using a Monochromatic X-Ray

In this method, the data obtained from the measured interference fringe patterns by conducting the phase restoration process thereon are line integral values of the spatial distribution of the phase shift amount. Then, it is possible to make the coordinate conversion on the projection data $p(\gamma, \eta)$ measured in any geometrical system $(\gamma, \eta)$ into the projection data $g(\mu,\beta)$ of the imaginary 360 degrees circular orbit fan beam CT, and then, in the similar manner to the discussion made heretofore, it comes to the condition for enabling to exactly reconstruct the ROI that the converted data $g(\mu,\beta)$ satisfies the uniqueness of the solution. Accordingly, the uniqueness of the solution is completely same to, and all of the conclusions made by the present invention can be established.

(2) Method by X-ray Phase Microscope or Talbot Type Interferometer with using Diffraction Grating In this method, the projection data obtained from an interference fringe pattern and/or a moire infringe pattern measured by conducting phase restoration process thereon comes to the data, being obtained by treating $1^{st}$ order differentiation on the line integral value of the phase shift amount spatial distribution into the direction perpendicular to each light beam (being called by differentiated phase projection data). Now, the differentiated phase projection data measured in an arbitrary geometrical system $(\gamma, \eta)$ is presented by $p^D(\gamma, \eta)$, and a unit normal vector in the direction, into which each data is differentiated, is $n(\gamma, \eta)$, the following relationship is established between each data $p^D(\gamma, \eta)$ and the differentiation filter projection data $g^D(\mu, \beta)$ of the equation (1) appearing in the Katsevich's FBP method corresponding to the same straight line.

[Equation 6]

$$g^D(u, \beta) = \frac{R}{\sqrt{R^2 + u^2}} (n(\gamma, \eta) \cdot a'(\beta)) p^D(\gamma, \eta) \qquad (6)$$

Figure 18:
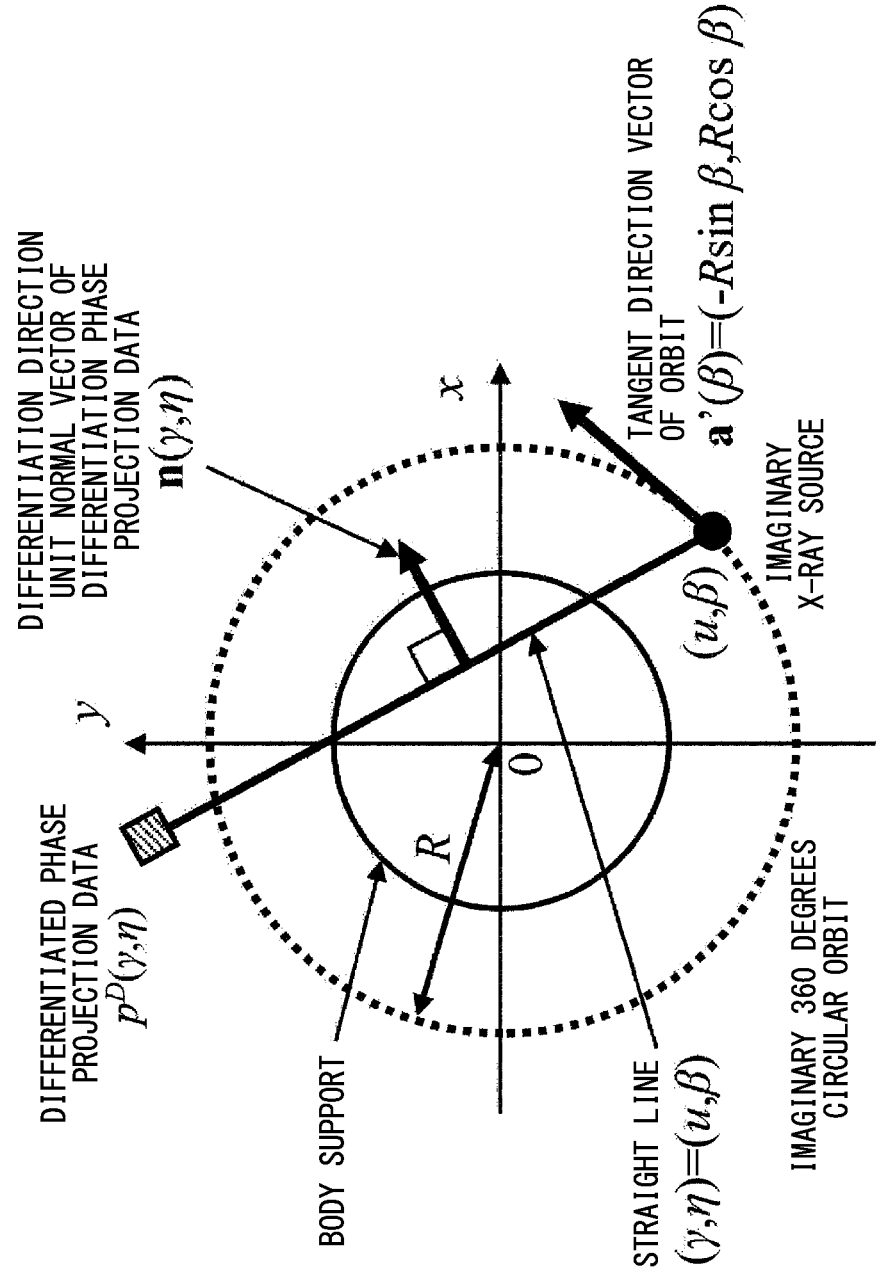
FIG. 18 is a view for showing the geometrical relationship in the X-ray phase microscope with using a diffraction grating therein, or in the method by a Talbot type interferometer.

However, $a'(\beta)$ is defined by $a'(\beta) \equiv (d/d\beta a(\beta)) = (-R\sin\beta, R\cos\beta)$. The proof of the equation (6), please refer to the Non-patent Document [11]. Further, in FIG. 18 is shown the geometrical relationship of the equation (6).

Accordingly, it is possible to convert the differentiated phase projection data $p^D(\gamma, \eta)$, which is measured in the arbitrary geometrical system, by using the equation (6), into the differentiated projection data $g^D(\mu, \beta)$ of Katsevich's FBP method in the imaginary 360 degrees circular orbit fan beam CT, in the similar manner to the discussion made heretofore, that the converted data $g^D(\mu, \beta)$ satisfies the uniqueness of the solution comes to the condition for enabling the exact reconstruction of ROI. Accordingly, the uniqueness of the solution is completely same to, and all of the conclusions are established.

As was mentioned in details in the above, the present invention is a more generalized interior CT image generation method which enables the image reconstruction at far high accuracy comparing to the conventional approximating solution, by means of the exact solution, even in the case where it is not in the situation that the prior information is already known, and said method is applicable to any CT imaging apparatuses upon basis the principle of generating the image from the physical quantity distribution by measuring the line integral values of the physical quantity distribution in the inside of the body.

However, generally, CT indicates the absorption X-ray CT of generating the X-ray absorption coefficient distribution as the image, in many cases, and therefore hereinafter, the explanation will be given, generally, on the X-ray CT apparatus for obtaining a section image of an inside of the body to be inspected, as the most general example of applying the image generation method of the present invention therein, by referring to the drawings.

Figure 19:
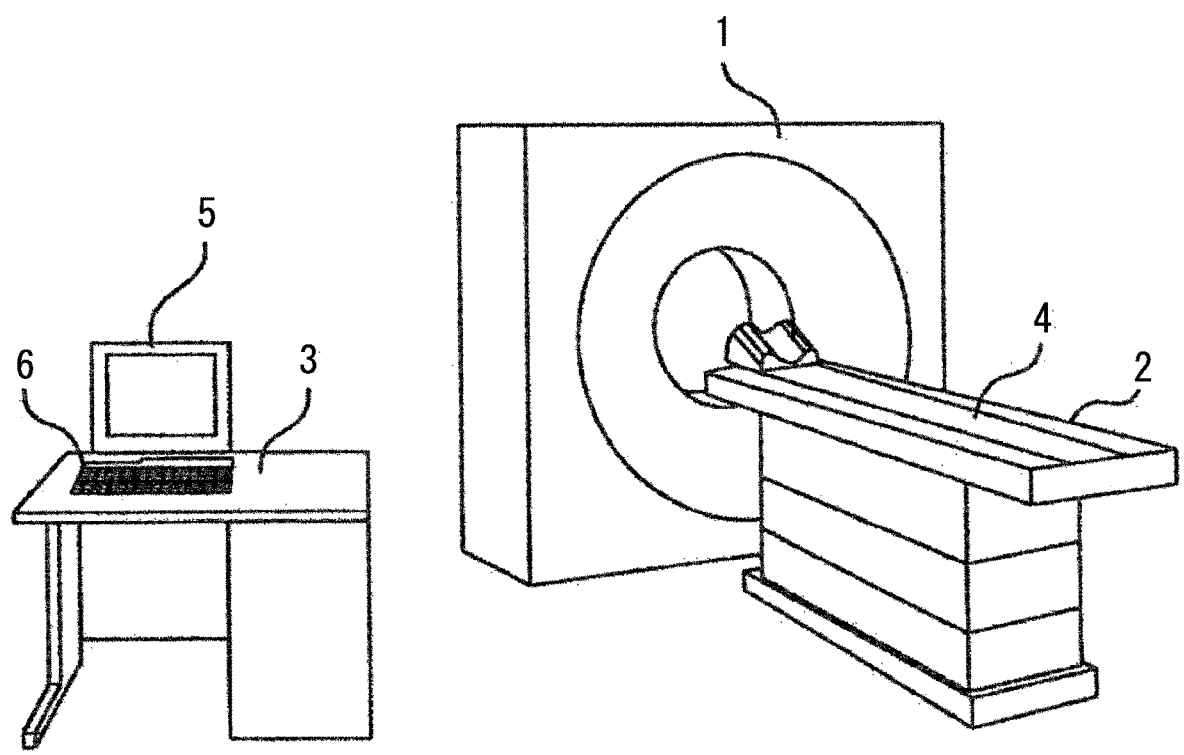
FIG. 19 is a view for showing external structure of an ordinary X-ray CT apparatus, as an example of the apparatus of utilizing the image reconstructing method according to the present invention therein.

FIG. 19 shows the entire outlook structure of a common X-ray CT apparatus for generating the physical quantity distribution in the form of the image through the data processing by measuring the line integral values of the physical quantity distribution in the inside of the body with using the image generation method mentioned above. Thus, the X-ray CT apparatus, while receiving therein the constituent elements of the X-ray radiating portion and so on, which will be mentioned below, comprises a gantry portion 1 having a cylinder-like cavity portion, into a central portion of which the object to be inspected is positioned, a base portion 2 having a cradle 4 for positioning the object to be inspected on an upper surface thereof, and a console portion 3 including computers as the data processing apparatus (not illustrated herein), a display device 5 for displaying the obtained images, etc., thereon, and a keyboard 6 for conducting necessary input therethrough, etc.

Figure 20:
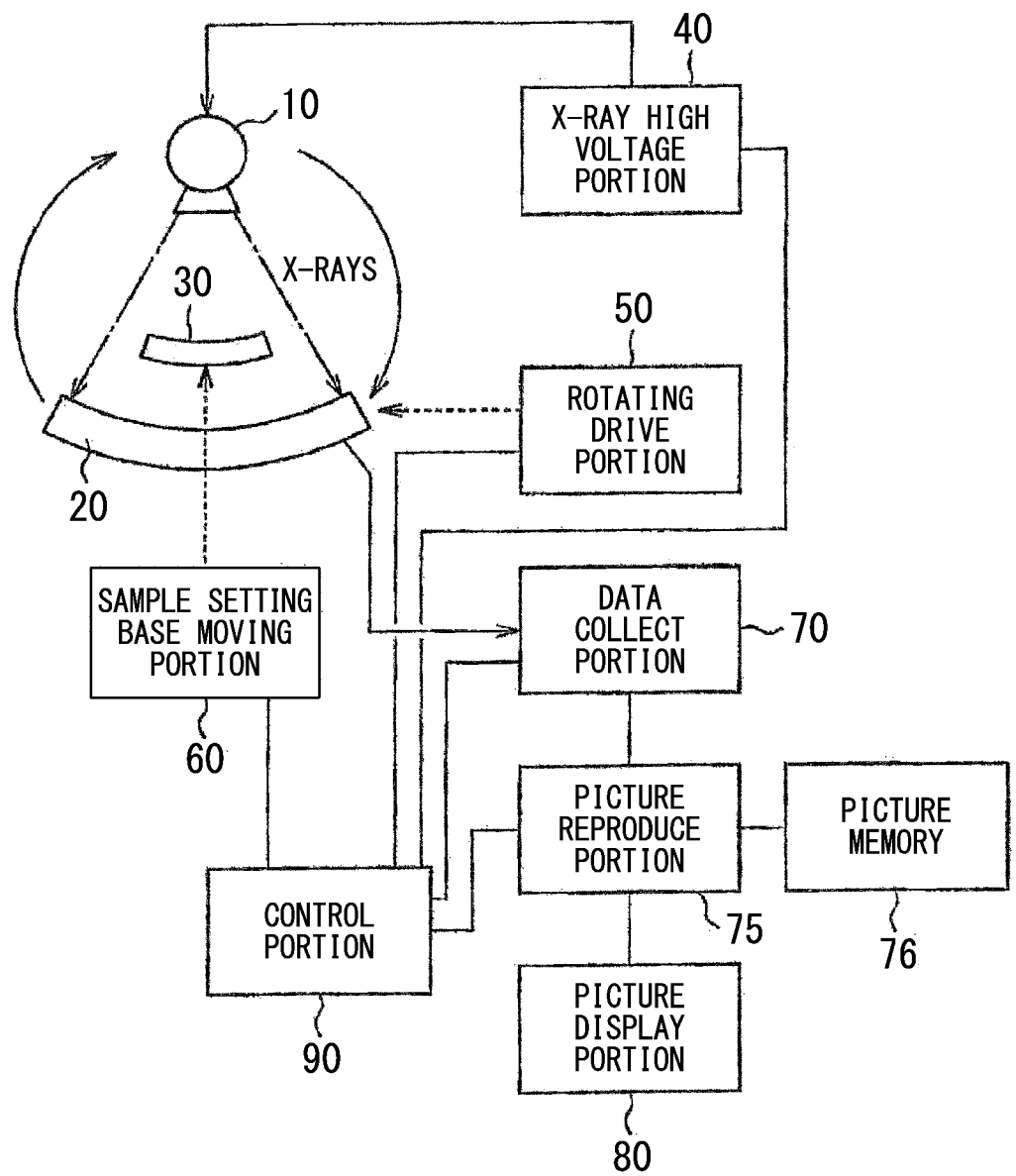
FIG. 20 is a view for showing an example of an interior structure of the X-ray CT apparatus mentioned above.

Within the housing of the gantry portion 1 or the console portion 3, as is shown in FIG. 20, there are provided constituent elements for constructing the X-ray CT apparatus. As an example thereof, as is illustrated, in an inside of the housing, there are provided an X-ray generating apparatus 10 for radiating the X-rays in a fan-like manner to the sample, an arc-like X-ray detecting apparatus 20 for detecting the X-rays radiated from said apparatus and passing through the body to be inspected, and wherein, not illustrated herein, it is attached on a ring-like frame, for example.

On the other hand, in a space between the X-ray generating apparatus 10 and the X-ray detecting apparatus 20 is provided a top board 30 (corresponding to the reference numeral 4 in FIG. 19) for setting the body to be inspected on an upper surface thereof. However, a member attaching the X-ray generating apparatus 10 and the X-ray detecting apparatus 20 in part thereof rotates into a predetermined direction at a predetermined velocity (refer to arrows in the figure), through a rotation driver portion 50, for example, by means of rotating driver mechanism, such as a motor, etc., provided in an inside of the gantry portion 1 mentioned above. On the other hand, the top board 30 for mounting the body to be inspected thereon is positioned to face to the above mentioned X-ray generating apparatus 10 and to the cylindrical space at around a central portion of the X-ray detecting apparatus 20, and is moved by the function of a sample mounting base moving portion 60. Further, on the gantry portion 1 are provided an X-ray high voltage portion 40 for generating high voltage to supply it to the X-ray generating apparatus 10 mentioned above, the rotation driver portion 50, etc., for rotationally driving the member, on which the X-ray generating apparatus 10 and the X-ray detecting apparatus 20 are attached, through the rotation control of the motor.

The detection signal from the X-ray detecting apparatus 20 is inputted to a data collecting portion 70 to be collected as the image data, and further, is reproduced in an image reproducing portion 75, as a section image of the inside of a sample or 3 dimensional image, etc. However, the reference numeral 76 depicts memory apparatus (image memory) to be used when reproducing the section image of the inside of the sample or the 3 dimensional image in the image reproducing portion 75. Also, the section image of the inside of the sample or the 3 dimensional image reproduced in said image reproducing portion 75 is displayed, for example, on an image display portion 80 (corresponding to the reference numeral 5 in FIG. 19), which is constructed with a liquid crystal display device, etc. Further, by combining so called a touch panel (not shown in the figure) to this image display portion 80, it is possible to do a necessary input to operate the apparatus by means of said image display portion 80. However, the present invention should not restricted to this; but in the place of said apparatus, there may be provide the keyboard (corresponding to reference numeral 6 in FIG. 19) and/or a ten keys or a mouse and so on.

The reference numeral 90 in the figure shows the control portion (corresponding to the reference numeral 3 in FIG. 19) for controlling an operation of each portion constructing the X-ray CT apparatus mentioned above. In more details, it is constructed by a central processing unit (CPU), and the memory devices (memory), such as RAM and/or ROM, for example, and further external memory devices, such as HDD, etc., and the necessary control is executed upon basis of software or firmware for controlling the operation of each portion, which are stored within the memory device(s).

And, the image generation method of the interior CT which is the present invention mentioned above is stored in the memory apparatus (memory), such as, RAM or ROM as the software, for example, in the image reproducing portion 75 constructing the X-ray CT apparatus mentioned above.

Further, the technology, into which the present invention can be applied, is not limited to this, it is applicable, for example, to the phase X-ray CT for generating the image of the phase shift distribution from the line integral data of the phase shift distribution when radiating the X-rays, PET (positron emission CT) and/or SPET (single photon emission type CT), being a nuclear medicine imaging apparatus for generating the image of distribution of radiopharmaceutical dosed into the body, CT of using an ultrasonic wave, micro wave, sonic wave, seismic wave, etc., electron CT, MRI (nuclear magnetic resonance imaging) utilizing the image reconstruction from the projection data, etc. Thus, "body" or "image" in the present invention indicates the spatial distribution of the physical quantity applied to imaging, and "projection data" indicates the measured data for presenting the line integral values on that straight line.

Also, the numerical values of the projection data including the phase shift, the phase shift of quantum beam, diffraction, or diffraction therein are extracted from a set of single number or plural number of projection data(s), which are obtained due to addition or position change of an optical element(s), and it is also possible to reconstruct the image with using the phase shift of said quantum beam that is extracted, diffraction, or the numerical values of said projection data including diffraction.

In the above, detailed description was made on the image generation method of the interior CT according to various embodiments of the present invention. However, the present invention should not be restricted to those embodiments mentioned above; but may include various variation (s) thereof. For example, the embodiments mentioned above are given on the system as a whole, for explaining the present invention, easily understandable, but it should not be limited, necessarily, only to that having all of the constituent elements explained in the above. Also, it is possible to add the constituent element (s) of other embodiment (s) to the constituent elements of a certain embodiment. Further, to/from/for a part of the constituent elements of each embodiment can be added/deleted/substituted other constituent element (s).

Figure 21:
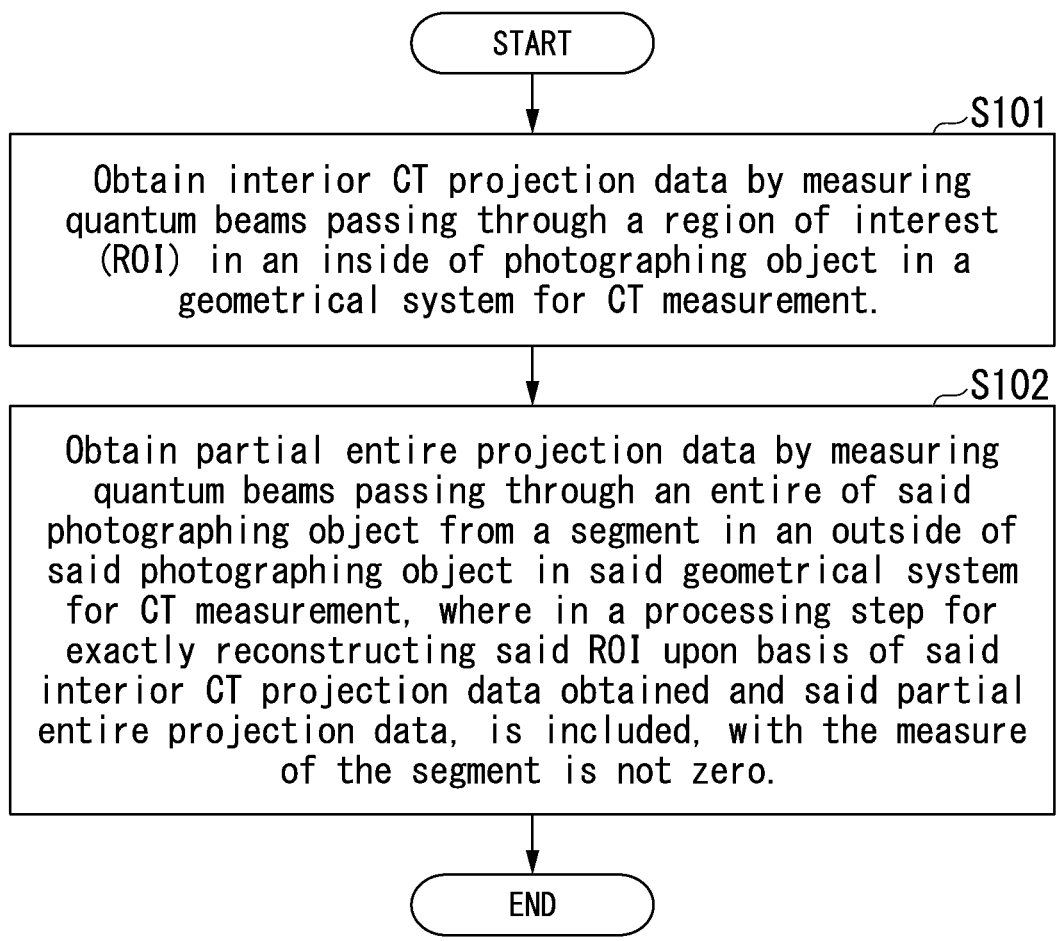
FIG. 21 is a flowchart showing an example of a flow of a process executed in the interior CT of the embodiment.

FIG. 21 is a flowchart showing an example of a flow of a process executed in the interior CT of the embodiment. Interior CT projection data is obtained by measuring only all of quantum beams passing through a region of interest (ROI) in an inside of photographing object in a geometrical system for CT measurement (step S101). Partial entire projection data is obtained by measuring quantum beams passing through an entire of said photographing object from a segment in an outside of said photographing object in said geometrical system for CT measurement, where in a processing step for exactly reconstructing said ROI upon basis of said interior CT projection data obtained and said partial entire projection data is included (step S102). And the measurement of the segment is not zero.

Figure 22:
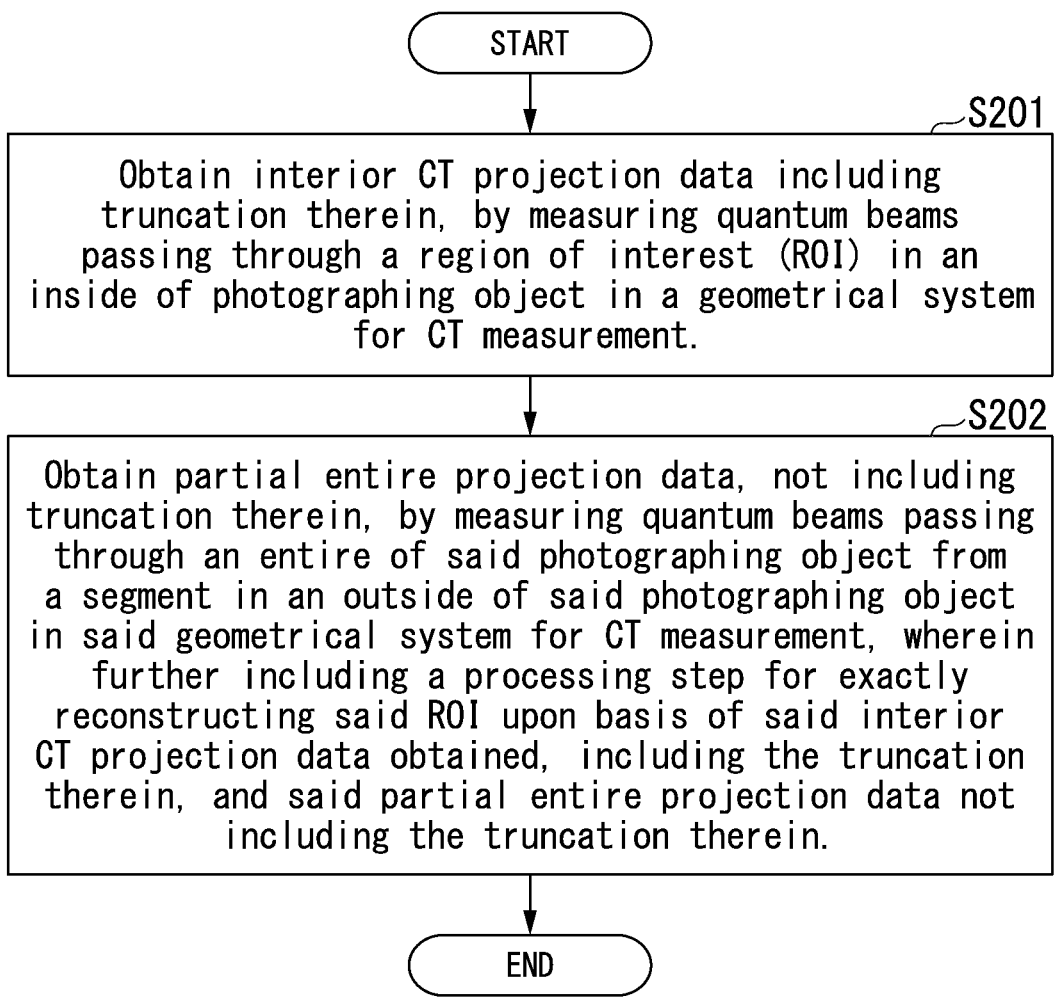
FIG. 22 is a flowchart showing an example of a flow of a process executed in the interior CT of the embodiment.

FIG. 22 is a flowchart showing an example of a flow of a process executed in the interior CT of the embodiment. Interior CT projection data is obtained including truncation therein, by measuring only all of quantum beams passing through a region of interest (ROI) in an inside of photographing object in a geometrical system for CT measurement (step S201). Partial entire projection data, not including truncation therein, is obtained by measuring quantum beams passing through an entire of said photographing object from a segment in an outside of said photographing object in said geometrical system for CT measurement, wherein further including a processing step for exactly reconstructing said ROI upon basis of said interior CT projection data obtained, including the truncation therein, and said partial entire projection data not including the truncation therein (step S202).

INDUSTRIAL APPLICABILITY

The present invention provides the image reconstructing method for generating the image from the physical quantity distribution by measuring the line integral values of the physical quantity distribution in the inside of the object or body, and in particular, provides the image reconstructing method of the interior CT.

EXPLANATION OF THE MARKS

1 . . . gantry portion, 3 . . . console portion, 4, 30 . . . top board, 10 . . . X-ray generating apparatus, 20 . . . X-ray detecting apparatus, 90 . . . control portion

The invention claimed is:

1. An image generation method of an interior CT comprising the following steps:
a step for obtaining interior CT projection data by measuring only all of quantum beams passing through a region of interest (ROI) in an inside of photographing object in a geometrical system for CT measurement;
a step for obtaining partial entire projection data by measuring quantum beams passing through an entire of said photographing object from a segment in an outside of said photographing object in said geometrical system for CT measurement; and
a processing step for exactly reconstructing said ROI upon basis of said interior CT projection data obtained and said partial entire projection data, wherein the measurement of said segment is not zero.

2. An image generation method of an interior CT according to claim 1, wherein said segment is an odd number (1,3,5, . . . ) of pieces of segments including a plural number of points corresponding to a curved line surrounding said photographing object therein.

3. An image generation method of an interior CT according to claim 2, wherein said interior CT projection data obtaining step is conducted by a 360 degrees circular orbit fan beam, and said partial obtaining of the entire projection data is conducted by a fan beam from said segment included in a circular orbit of said 360 degrees circular orbit fan beam for obtaining said interior CT projection data.

4. An image generation method of an interior CT according to claim 2, wherein said interior CT projection data obtaining step is conducted by a fan beam short scan, said partial entire projection data obtaining is conducted by fan beam from said segment included in an arc orbit of said fan beam short scan for obtaining said interior CT projection data.

5. An image generation method of an interior CT according to claim 2, wherein said interior CT projection data obtaining step is conducted by a 180 degrees parallel beam scan, and said partial entire projection data obtaining is conducted by parallel beams from said segment included in an orbit of said 180 degrees parallel short beam scan for obtaining said interior CT projection data.

6. An image generation method of an interior CT according to claim 3, wherein said segment is so set that at least one or more projection data is included in an angle thereof.

7. An image generation method of an interior CT according to claim 1, wherein said reconstructing processing step of ROI is executed by any one of an analytic image reconstructing method, a successive approximation image reconstructing method and a statistic image reconstructing method, or a combination of those.

8. An image generation method of an interior CT according to claim 1, wherein an aperture angle of quantum beams for obtaining said interior CT projection data and said partial entire projection data is controlled by using an active collimator.

9. An image generation method of an interior CT according to claim 1, wherein as said partial entire projection data, a Scout-View scan projection data is used.

10. An image generation method of an interior CT according to claim 1, wherein said partial entire projection data is obtained with using measurement of radiating other quantum beams having spatial resolution, which is lower than said interior CT projection data.

11. An image generation method of an interior CT according to claim 1, wherein said interior CT projection data and said entire projection data measured by radiating quantum beams on an object are line integrals of spatial distribution of physical quantities of at least any one of absorption, phase shift, scattering, diffraction and refraction, which are caused due to mutual interaction between quantum beam and an object, on a straight line, along which said quantum beams pass through.

12. An image generation method of an interior CT comprising the following steps:

a step for obtaining interior CT projection data including truncation therein, by measuring only all of quantum beams passing through a region of interest (ROI) in an inside of photographing object in a geometrical system for CT measurement;

a step for obtaining partial entire projection data, not including truncation therein, by measuring quantum beams passing through an entire of said photographing object from a segment in an outside of said photographing object in said geometrical system for CT measurement; and a processing step for exactly reconstructing said ROI upon basis of said interior CT projection data obtained, including the truncation therein, and said partial entire projection data not including the truncation therein.

13. An image generation method of an interior CT according to claim 12, wherein said reconstruction processing step of ROI is executed by any one of an analytic image reconstructing method, a successive approximation image reconstructing method and a statistic image reconstructing method, or a combination of those.

14. An image generation method of an interior CT according to claim 12, wherein inability of calculation of Hilbert transform in said interior CT projection data including said truncation therein is brought into ability of calculation by using said partial entire projection data not including said truncation therein, and thereby reconstructing said ROI.

* * * * *